United States Patent [19]

Delorme et al.

[11] Patent Number: 5,552,437
[45] Date of Patent: Sep. 3, 1996

[54] BISARYLCARBINOL DERIVATIVES AS INHIBITORS OF LEUKOTRIENE BIOSYNTHESIS

[75] Inventors: Daniel Delorme; Daniel Dubé, both of St. Lazare; Yves Ducharme, Montreal; Erich L. Grimm, Baie d'Urfe; Richard Friesen, Dollard des Ormeaux; Carole Lepine, Laval, all of Canada

[73] Assignee: Merck Frosst Canada, Inc., Kirkland, Canada

[21] Appl. No.: 330,036

[22] Filed: Oct. 27, 1994

[51] Int. Cl.$^6$ .................. A61K 31/35; C07D 405/12
[52] U.S. Cl. .................. 514/457; 514/826; 549/289
[58] Field of Search .................. 549/289; 514/457, 514/826

[56] References Cited

FOREIGN PATENT DOCUMENTS

| | | |
|---|---|---|
| 381375 | 1/1989 | European Pat. Off. . |
| 0385662 | 9/1990 | European Pat. Off. . |
| 0462830 | 12/1991 | European Pat. Off. . |
| 0462812 | 12/1991 | European Pat. Off. . |
| 505122 | 3/1992 | European Pat. Off. . |
| WO94/00444 | 1/1994 | WIPO . |

OTHER PUBLICATIONS

J. Med. Chem., V. 35, 1992, pp. 2600–2609.
CA98: 179160, Merchant, Dep. Org. Chem., Inst. Sci., Bombay, 400 032, India (1982) (23) p. 955.

*Primary Examiner*—Sharon Gibson
*Assistant Examiner*—Catherine Kilby Scalzo
*Attorney, Agent, or Firm*—Mollie M. Yang; David L. Rose

[57] ABSTRACT

Compounds having the Formula I:

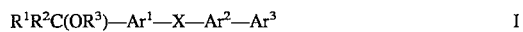

re inhibitors of leukotriene biosynthesis. These compounds are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

9 Claims, No Drawings

BISARYLCARBINOL DERIVATIVES AS INHIBITORS OF LEUKOTRIENE BIOSYNTHESIS

BACKGROUND OF THE INVENTION

The leukotrienes constitute a group of locally acting hormones, produced in living systems from arachidonic acid. The major leukotrienes are Leukotriene $B_4$ (abbreviated at $LTB_4$), $LTC_4$, $LTD_4$ and $LTE_4$. The biosynthesis of these leukotrienes begins with the action of the enzyme 5-lipoxygenase on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book *Leukotrienes and Lipoxygenases*, ed. J. Rokach, Elsevier, Amsterdam (1989). The actions of the leukotrienes in living systems and their contribution to various diseases states are also discussed in the book by Rokach.

EP 385,662 (published Sep. 5, 1990) discloses 5-lipoxygenase inhibitors of the formula

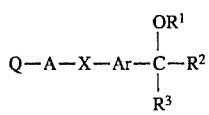

in which a heterocyclic moiety, Q, is linked to Ar, which may be phenylene, via A—X. The group $CR^2R^3$ attached to Ar represents a O—, S— or N-containing heterocyclic ring, whereas the $CR^1R^2$ of the present invention does not form a ring. The $Ar^3$ unit of the present invention is absent from the above formula.

EP 462,812 (published Dec. 27, 1991) discloses 5-lipoxygenase inhibitors of the formula

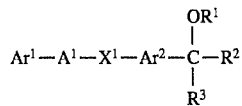

in which a phenyl, naphthyl or a bicyclic heterocycle ($Ar^1$) is linked to a 5-membered heterocycle ($Ar^2$) via $A^1$—$X^1$. The group $CR^2R^3$ attached to $Ar^2$ represents a O- or S-containing heterocyclic ring. The present compounds lack such a ring.

EP 462,830 (published Dec. 27, 1991) discloses 5-lipoxygenase inhibitors of the formula

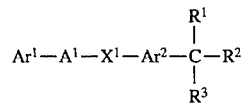

in which a phenyl, naphthyl or a bicyclic heterocycle ($Ar^1$) is linked to a phenylene or pyridylene ($Ar^2$) via $A^1$—$X^1$. The group $CR^2R^3$ attached to $Ar^2$ represents a O or S-containing heterocyclic ring; $R^1$ is for example H, alkyl, alkyocarbonyl, or alkylthio. In contrast, $CR^1R^2$ of the present compounds does not define a ring, and $OR^3$ on the present compounds is different from $R^1$ of the above formula.

WO94/00444 (published Jan. 6, 1994) discloses leukotriene biosynthesis inhibitors which are aryl substituted naphthalenes of the formula

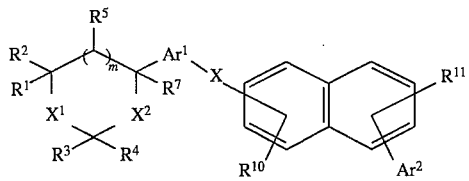

The present compounds differ from those of the above formula in that they lack the ring containing $X^1$ and $X^2$.

Crawley et al (*J. Med. Chem.* 1992, 35, 2600–2609) discloses the 5-lipoxygenase inhibitor of the formula below. The compounds of the present invention differ in that they lack the tetrahydropyran ring, and that they possess an aromatic substituent on the bicyclic ring moiety.

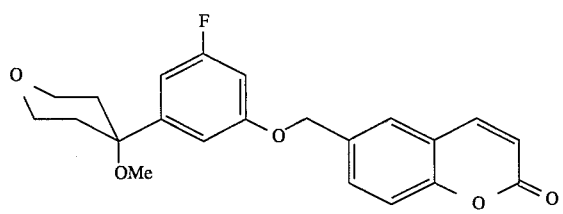

SUMMARY OF THE INVENTION

The present invention relates to compounds having activity as leukotriene biosynthesis inhibitors, to methods for their preparation, and to methods and pharmaceutical formulations for using these compounds in mammals (especially humans).

Because of their activity as leukotriene biosynthesis inhibitors, the compounds of the present invention are useful as anti-asthmatic, anti-allergic, anti-inflammatory, and cytoprotective agents. They are also useful in treating angina, cerebral spasm, glomerular nephritis, hepatitis, endotoxemia, uveitis, and allograft rejection and in preventing the formation of atherosclerotic plaques.

DETAILED DESCRIPTION OF THE INVENTION

The present invention provides compounds of Formula I

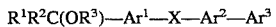

$$R^1R^2C(OR^3)\text{—}Ar^1\text{—}X\text{—}Ar^2\text{—}Ar^3 \qquad I$$

wherein:

$Ar^1$ is a 6-membered aromatic ring containing 0–3N, substituted with one or two of the same or different $R^4$ groups;

$Ar^2$ is a 10-membered bicyclic ring, substituted with one or two of the same or different $R^5$ groups, wherein said bicyclic ring is a bicyclic aromatic ring containing 0–4 ring N, 2H-1-benzopyran-2-one, or 2H-2-thioxo-1-benzopyran;

$Ar^3$ and $Ar^4$ are independently a 5-membered aromatic ring containing one O or S and 0–3N; a 5-membered aromatic ring containing 1–4N; or a 6-membered aromatic ring containing 0–3N; wherein said aromatic ring is substituted with one or two of the same or different $R^6$ groups;

X is $OCH_2$, $C_2O$, S, S(O), or $S(O)_2$;

$R^1$ is H, lower alkyl, lower perfluoroalkyl or $Ar^4$;

$R^2$ is H, lower alkyl or lower perfluoroalkyl;

$R^3$ is H or lower alkyl;

$R^4$ is H, lower alkyl, lower alkoxy, lower alkylthio, $NO_2$, CN, $CF_3$, $CF_3O$ or halogen;

$R^5$ is $R^4$, oxo or thioxo;

$R^6$ is $R^4$, lower alkylsulfinyl, lower alkylsulfonyl or $CO_2R^7$;

$R^7$ is H or lower alkyl;

or a pharmaceutically acceptable salt thereof.

A preferred embodiment of the present invention provides compounds of Formula I wherein:

$Ar^1$ is Phe or Pye, each of which is substituted with one or two of the same or different $R^4$ groups;

$Ar^3$ is Ph, Py, Fu, Th, Tz, Im, or Pyr, each of which is substituted with one or two of the same or different $R^6$ groups;

X is $OCH_2$, $CH_2O$, S, S(O), or $S(O)_2$;

$R^1$ is H, lower alkyl, lower perfluoroalkyl, Ph, Py, Im, Fu or Tz;

and the remaining substitutents are as defined above for Formula I.

A more preferred embodiment of the present invention provides compounds of Formula I wherein:

$Ar^1$ is Phe or Pye each of which is unsubstituted or substituted with halogen;

$Ar^2$ is naphthyl, quinolinyl, isoquinolinyl or 2H-1-benzopyran-2-one, wherein said naphthyl and quinolinyl are optionally substituted with CN;

$Ar^3$ is Ph, Py, Fu, Th, Tz, Im, or Pyr each of which is substituted with one or two of the same or different $R^6$ groups;

X is $OC_2$, $CH_2O$, S, S(O) or $S(O)_2$;

$R^1$ is H, lower alkyl, lower perfluoroalkyl, Ph, Py or Tz;

$R^6$ is $R^4$;

and the remaining substitutents are as defined above for Formula I.

DEFINITIONS

The following abbreviations have the indicated meanings:

Ac=acetyl
AIBN=2,2-azobisisobutyronitrile
Bn=benzyl
$Bu_4NF$=n-tetrabutylammonium fluoride
DMAP=4-(dimethylamino)pyridine
DMB=dimethoxybenzyl
DMF=N,N-dimethylformamide
DMSO=dimethyl sulfoxide
dppf=1,1'-bis(diphenylphosphino)ferrocene
$Et_3N$=triethylamine
Fu=2- or 3-furyl
Im=1-, 2-, 4-, or 5-imidazolyl
KHMDS=potassium hexamethyldisilazane
LAH=lithium aluminum hydride
LDA=lithium diisopropylamide
mCPBA=meta-chloroperoxybenzoic acid
Ms=methanesulfonyl=mesyl
MsO=methanesulfonate=mesylate
NBS=N-bromosuccinimide
NCS=N-chlorosuccinimide
NIS=N-iodosuccinimide
NMP=N-methyl-2-pyrrolidinone
NSAID=non-steroidal anti-inflammatory drug
PCC=pyridinium chlorochromate
PDC=pyridinium dichromate
Ph=phenyl
Phe=benzenediyl
Py=2-, 3- or 4-pyridyl
Pye=pyridinediyl
Pyr=2- or 3-pyrrolyl
r.t.=room temperature
rac.=racemic
SEM=trimethylsilylethoxymethyl
TBDMS=tert-butyldimethylsilyl
TBDPS=tert-butyldiphenylsilyl
Tf=trifluoromethanesulfonyl=triflyl
$Tf_2O$=trifluoromethanesulfonic anhydride
TFAA=trifluoroacetic anhydride
TfO=trifluoromethanesulfonate=triflate
Th=2- or 3-thienyl
THF=tetrahydrofuran
TLC=thin layer chromatography
Ts=p-toluenesulfonyl=tosyl
TsO=p-toluenesulfonate=tosylate
Tz=2-, 4- or 5-thiazolyl

ALKYL GROUP ABBREVIATIONS

Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Alkyl means linear, branched and cyclic structures and combinations thereof.

"Lower alkyl" means alkyl groups of from 1 to 7 carbon atoms. Examples of lower alkyl groups include methyl, ethyl, propyl, isopropyl, n-butyl, s- and t-butyl, pentyl, hexyl, heptyl, cyclopropyl, cyclobutyl, cyclohexyl and the like.

"Lower perfluoroalkyl" includes lower alkyl groups in which all the hydrogen atoms are replaced by fluorine. Examples are $-CF_3$, $-CF_2CF_3$, $c-Pr-F_5$, $c-Hex-F_{11}$ and the like.

"Lower alkoxy" means alkoxy groups of from 1 to 7 carbon atoms of a straight, branched, or cyclic configuration. Examples of lower alkoxy groups include methoxy, ethoxy, propoxy, isopropoxy, cyclopropyloxy, cyclohexyloxy, and the like.

"Lower alkylthio" means alkylthio groups of from 1 to 7 carbon atoms of a straight, branched or cyclic configuration. Examples of lower alkylthio groups include methylthio, propylthio, isopropylthio, cycloheptylthio, etc. By way of illustration, the propylthio group signifies $-SCH_2CH_2CH_3$.

"Lower alkylsulfinyl" means those alkylsulfinyl groups of from 1 to 7 carbon atoms of a straight, branched or cyclic configuration. Examples of lower alkylsulfinyl groups are methylsulfinyl, 2-butylsulfinyl, cyclohexylmethylsulfinyl, etc. By way of illustration the 2 -butylsulfinyl group signifies —S(O)CH(CH$_3$)CH$_2$CH$_3$.

"Lower alkylsulfonyl" means those alkylsulfonyl groups of from 1 to 7 carbon atoms of a straight, branched or cyclic configuration. Examples of lower alkylsulfonyl groups are methylsulfonyl, 2-butylsulfonyl, cyclohexylmethylsulfonyl, etc. By way of illustration the 2 -butylsulfonyl group signifies —S(O)$_2$CH(CH$_3$)CH$_2$CH$_3$.

Halogen includes F, Cl, Br, and I.

Examples of "6-membered aromatic ring containing 0–3N" include benzene, pyridine, pyridazine, pyrimidine, pyrazine, 1,2,3 -triazine, 1,2,4-triazine and 1,3,5-triazine.

Examples of "10-membered bicyclic aromatic ring containing 0–4N" include naphthalene, quinoline, isoquinoline, cinnoline, quinazoline, quinoxaline, naphthyridine, and pteridine.

Examples of "5-membered aromatic ring containing one O or S and 0–3N" include furan, oxazole, isoxazole, 1,2,5 -oxadiazole, 1,3,4-oxadiazole, thiophene, thiazole, isothiazole, 1,2,4 -thiadiazole and 1,3,4-thiadiazole.

Examples of "5-membered aromatic ring containing 1–4N" include pyrrole, pyrazole, imidazole, 1,2,3-triazole, 1,2,4-triazole and tetrazole.

Optical Isomers—Diastereomers—Geometric Isomers

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Salts

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, mannganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

Utilities

The ability of the compounds of Formula I to inhibit biosynthesis of the leukotrienes makes them useful for preventing or reversing the symptoms induced by the leukotrienes in a human subject. This inhibition of the mammalian biosynthesis of leukotrienes indicates that the compounds and pharmaceutical compositions thereof are useful to treat, prevent, or ameliorate in mammals and especially in humans: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) intimation such as arthritis or inflammatory bowel disease, 4) pain, 5) skin disorders such as atopic eczema, and the like, 6) cardiovascular disorders such as angina, formation of atherosclerotic plaques, myocardial ischemia, hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, and 17) proliferation of myoblastic leukemia cells.

Thus, the compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as CCl$_4$ and D-galactosamine; ischemic renal failure; disease-induced hepatic damage; bile salt induced pancreatic or gastric damage; trauma- or stress-induced cell damage; and glycerol-induced renal failure. The compounds also act as inhibitors of rumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like.

Two assays can be used to measure cytoprotective ability. These assays are; (A) an ethanol-induced lesion assay and (B) an indomethacin-induced ulcer assay and are described in EP 140,684.

Dose Ranges

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

For use where a composition for intravenous administration is employed, a suitable dosage range for anti-asthmatic, anti-inflammatory, or anti-allergic use is from about 0.001 mg to about 25 mg (preferably from 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for ant-asthmatic, anti-inflammatory or anti-allergic use is, e.g. from about 0.01 mg to about 100 mg of a compound of Formula I per kg of body weight per day, preferably from about 0.1 mg to about 10 mg per kg and for cytoprotective use from 0.1 mg to about 100 mg (preferably from about 1 mg to about 100 mg and more preferably from about 10 mg to about 100 mg) of a compound of Formula I per kg of body weight per day.

For the treatment of diseases of the eye, ophthalmic preparations for ocular administration comprising 0.001–1% by weight solutions or suspensions of the compounds of Formula I in an acceptable ophthalmic formulation may be used.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with an NSAID that might otherwise cause such damage (for example, indomethacin). For such use, the compound of Formula I is administered from 30 min. prior up to 30 minutes after administration of the NSAID. Preferably it is administered prior to or simultaneously with the NSAID, (for example, in a combination dosage form).

Pharmaceutical Compositions

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

Suitable topical formulations of a compound of Formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral s liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liquid Concentrate | 1.2 mg |
| Trichlorofluoromethane, NF | 4.025 gm |
| Dichlorodifluoromethane, NF | 12.15 gm |

Combinations With Other Drugs

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:

(1) propionic acid derivatives;

(2) acetic acid derivatives;

(3) fenamic acid derivatives;

(4) oxicams; and (5) biphenylcarboxylic acid derivatives, or a pharmaceutically acceptable salt thereof.

The propionic acid derivatives which may be used comprise: alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, prano-profen, suprofen, tiaprofenic acid, and tioxaprofen. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH$_3$)COOH or —CH$_2$CH$_2$COOH group (which optionally can be in the form of a pharmaceutically acceptable salt group, e.g., —CH(CH$_3$)COO$^-$Na$^+$ or —CH$_2$CH$_2$COO$^-$Na$^+$), typically attached directly or via a carbonyl function to a ring system, preferably to an aromatic ring system.

The acetic acid derivatives which may be used comprise: indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac. Structually related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH$_2$COOH group (which optionally can be in the form of a pharmaceutically acceptable salt group, e.g.—CH$_2$COO$^-$Na$^+$), typically attached directly to a ring system, preferably to an aromatic or heteroaromatic ring system.

The fenamic acid derivatives which may be used comprise: flufenamic acid, meclofenamic acid, mefenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

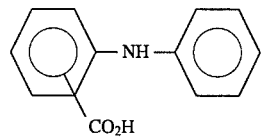

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

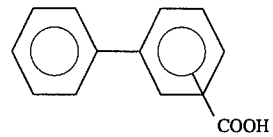

which can bear a variety of substituents and in which the free —COOH group can be in the form of a pharmaceutically acceptable salt group, e.g., —COO$^-$Na$^+$.

The oxicams which can be used in the present invention comprise: isoxicam, piroxicam, sudoxicam and tenoxican. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

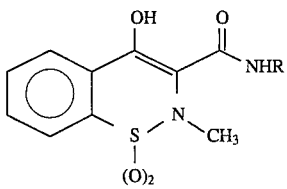

wherein R is an aryl or heteroaryl ring system.

The following NSAIDs may also be used: amfenac sodium, aminoprofen, anitrazafen, antrafenine, auranofin, bendazac lysinate, benzydanine, beprozin, broperamole, bufezolac, cinmetacin, ciproquazone, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclorac, fendosal, fenflumizole, feprazone, floctafenine, flunixin, flunoxaprofen, fluproquazone, fopirtoline, fosfosal, furcloprofen, glucametacin, guaimesal, ibuproxam, isofezolac, isonixim, isoprofen, isoxicam, lefetamine HCl, leflunomide, lofemizole, lonazolac calcium, lotifazole, loxoprofen, lysin clonixinate, meclofenamate sodium, meseclazone, nabumetone, nictindole, nimesulide, orpanoxin, oxametacin, oxapadol, perisoxal citrate, pimeprofen, pimetacin, piproxen, pirazolac, pirfenidone, proglumetacin maleate, proquazone, pyridoxiprofen, sudoxicam, talmetacin, talniflumate, tenoxicam, thiazolinobutazone, thielavin B, tiaramide HCl, tiflamizole, timegadine, tolpadol, tryptamid, and ufenamate.

The following NSAIDs, designated by company code number (see e.g., *Pharmaprojects*), may also be used: 480156S, AA861, AD1590, AFP802, AFP860, AI77B, AP504, AU8001, BPPC, BW540C, CHINOIN 127, CN100, EB382, EL508, F1044, GV3658, ITF182, KCNTEI6090, KME4, $LA_{2851}$, MR714, MR897, MY309, $ONO_{3144}$, $PR^{823}$, PV102, PV108, R830, RS2131, SCR152, SH440, $SIR^{133}$, SPAS510, SQ27239, ST281, SY6001, TA60, TAI-901 (4-benzoyl-1-indancarboxylic acid), TVX2706, U60257, UR2301, and WY41770.

Finally, NSAIDs which may also be used include the salicylates, specifically acetyl salicylic acid and the phenylbutazones, and pharmaceutically acceptable salts thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin. Pharmaceutical compositions comprising the Formula I compounds may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of the Formula I may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058, 785 (Apr. 15, 1981), which are hereby incorporated herein by reference.

Pharmaceutical compositions comprising the Formula I compounds may also contain as the second active ingredient, prostaglandin antagonists such as those disclosed in EP 11,067 (May 28, 1980) or thromboxane antagonists such as those disclosed in U.S. Pat. No. 4,237,160. They may also contain histidine decarboxylase inhibitors such as α-fluoromethylhistidine, described in U.S. Pat. No. 4,325,961. The compounds of the Formula I may also be advantageously combined with an $H_1$ or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Compounds of Formula I may also be usefully combined with most cell stabilizing agents, such as 1,3-bis(2-carboxychromon-5-yloxy)-2 -hydroxypropane and related compounds described in British Patent Specifications 1,144,905 and 1,144,906. Another useful pharmaceutical composition comprises the Formula I compounds in combination with serotonin antagonists such as methysergide, the serotonin antagonists described in *Nature*, 316, 126–131 (1985), and the like. Each of the references referred to in this paragraph is hereby incorporated herein by reference.

Other advantageous pharmaceutical compositions comprise the Formula I compounds in combination with anticholinergics such as ipratropium bromide, bronchodilators such as the beta agonist salbutamol, metaproterenol, terbutaline, fenoterol and the like, and the anti-asthmatic drugs theophylline, choline theophyllinate and enprofylline, the calcium antagonists nifedipine, diltiazem, nitrendipine, verapamil, nimodipine, felodipine, etc. and the corticosteroids, hydrocortisone, methylprednisolone, betamethasone, dexamethasone, beclomethasone, and the like.

Methods Of Synthesis

Compounds of Formula I of the present invention may be prepared according to the synthetic routes outlined in Schemes 1 to 13 and by the following methods described herein.

Scheme 1

Compounds of Formulas 1A and 1B can be synthesized using the route described in Scheme 1. Bromophenol H can be acetylated by treating a mixture of II and acetyl chloride in the presence of a base such as pyridine in a solvent such as dichloromethane to yield the corresponding acetate which, upon heating neat with a Lewis acid such as aluminum chloride, gives the acyl derivative III. Reaction of III with first an inorganic base such as sodium hydride in an organic solvent such as benzene followed by addition of a carbonate such as diethylcarbonate furnishes the intermediate IV. The intermediate IV is then transformed using trifluoromethanesulfonic anhydride, in the presence of an amine such as triethylamine, in a neutral solvent such as dichloromethane, to the corresponding triflate V. Cross coupling of this material with an aryl lithium species resulting from reaction of an aryl halide (Br or I) with an alkyl lithium such as n-BuLi in a mixture of THF/hexanes, in the presence of trimethyl borate and catalyzed by a Pd(0) species such as $(Ph_3P)_4Pd$, in a mixture of THF/water as solvent, affords derivatives VI. Compounds of Formula 1A can be obtained by heating a mixture of VI and a thiophenol of general structure VII (Scheme 10) in a polar solvent such as N-methyl-2-pyrrolidinone with an inorganic base like potassium carbonate.

Compounds of Formula 1B can be obtained by treating compounds of general structure 1A in the presence of a peracid such as mCPBA in an organic solvent such as dichloromethane.

Scheme 2

Compounds of Formula 1C can be synthesized using the route described in Scheme 2. The meta-cresol VIII is converted in several steps to the Compound IX using the same protocol as described in Scheme 1 for the conversion of II to VI. Intermediate IX is then brominated by heating in the presence of a brominating reagent such as NBS in an organic solvent such as carbon tetrachloride in the presence of a catalytic amount of a radical initiator such as AIBN, giving access to Compound X. Bromide displacement can be accomplished using a phenol of a general structure XI (Scheme 9) in the presence of an inorganic base such as cesium carbonate in an aprotic dipolar solvent such as DMF to afford compounds of Formula 1C.

Scheme 3

Compounds of Formula 1D can be prepared as shown in Scheme 3. The aromatic bromide VI can be reacted by heating in the presence of trimethylsilylethane thiol and an inorganic base such as potassium carbonate in a polar solvent such as N-methyl-2-pyrrolidinone to afford derivative XII. The thiol derivatives XIII can be obtained by treating XII with $Bu_4NF$ in an organic solvent such as DMF. Sulfur linked compounds may be obtained by heating thiol XIII with an aromatic bromide of general formula XIV (Scheme 13) in the presence of an inorganic base such as potassium carbonate in a polar solvent such as N-methyl-2-pyrrolidinone to yield compounds of Formula 1D.

Scheme 4

Compounds of Formula 1E, IF and IG can be obtained using the route described in Scheme 4. Naphthalene XV (U.S. Pat. No. 5,308,852, Merck Frosst) can be transformed to the corresponding triflate XVII using trifluoromethanesulfonic anhydride in the presence of a tertiary amine such as triethylamine in a neutral solvent such as dichloromethane. The resulting triflate can be reacted with a palladium (II) species such as palladium acetate, a catalyst such as 1,1'-bis(diphenylphosphino)ferrocene, an organic base (e.g. $Et_3N$) and methanol in a dipolar aprotic solvent (for example DMSO) under an atmosphere of carbon monoxide to yield XVIII. The ester function in XVIII can be selectively reduced to the primary alcohol XIX using lithium borohydride in an organic solvent such as THF. Coupling products of structures IE and IF can be obtained by reacting the phenol XV with compounds of the general structure XVI (Schemes 11 and 12), and the alcohol XIX with compounds of general structure XI (Scheme 2), respectively, using a phosphine such as triphenylphosphine in the presence of an azodicarboxylate (e.g. dimethylazodicarboxylate) in an organic solvent such as THF. The coupling reaction between alcohol XIX and the general structure XIV (Scheme 13) to obtain compound IG can be effected using a base such as sodium hydroxide and 18-crown-6 in a hot organic solvent such as toluene.

Scheme 5

Compounds of Formula 1H can be obtained using the route described in Scheme 5. The triflate XVII can be transformed to the trimethyltin derivative XX using a ditin such as hexamethylditin in the presence of palladium (0) species such as tetrakis(triphenylphosphine) palladium and in the presence of lithium chloride. Iodination of XX to the corresponding iododerivative XXI can be done by treating XX with iodine in an organic solvent such as chloroform. Final products of the general structure 1H can be obtained by coupling the iododerivative XXI with the thiophenol of the general structure VII (Scheme 10) in the presence of a base such as potassium tert-butoxide, and a palladium (0) species such as tetrakis(triphenyl-phosphine) palladium, in a hot solvent such as ethanol.

Scheme 6

Compounds of the Formula 1J can be synthesized as shown in Scheme 6. The iododerivative XXI can be treated with trimethylsilylethanethiol in the presence of potassium tert-butoxide and a palladium (0) species such as tetrakis(triphenylphosphine) palladium in a hot protic solvent such as ethanol giving compounds XXII. Deprotection of XXII using a fluoride source such as tetrabutylammonium fluoride in an organic solvent such as THF gives the corresponding thiol XXIII. Coupling reaction between the thiol XXIII and the bromoderivative of the general structure XIV (Scheme 13) in the presence of an inorganic base such as potassium carbonate in an organic solvent such as DMF and N-methyl-2-pyrrolidinone gives Compound 1J.

Scheme 7

The quinoline 1K of Scheme 7 may be prepared in a multistep sequence from an appropriately dihalogenated quinoline XXIV. The quinoline XXIV is firstly convened into the quinoline XXV by a regioselective reaction with an appropriate metalated aromatic such as dimethyl 3-furyl borate in the presence of a catalyst such as tetrakis(triphenylphosphine)palladium. The conversion to the quinoline XXVI is achieved by treatment of XXV with a metalated methyl reagent such as methyl magnesium bromide in the presence of a catalyst such as [1,3 -bis(diphenylphosphino) propane]nickel (II) chloride. The quinoline XXVI is convened into the quinoline XXVII by first treatment with an oxidizing reagent such as m-chloroperoxybenzoic acid in an organic solvent followed by reaction of the intermediate N-oxide with an acylating reagent such as dialkylcarbamyl chloride, and a cyanating agent such as trimethylsilyl cyanide. Bromination of XXVII is achieved upon treatment with a bromine source, such as N-bromosuccinimide and light. Coupling of the benzylic halide XXVIII with the appropriate phenol of the general structure XI (Scheme 9) in an organic solvent such as DMF using an inorganic base such as $Cs_2CO_3$ provides compounds of formula 1K of the present invention.

Scheme 8

The isoquinoline 1L of Scheme 8 may be prepared in a multi-step sequence from an appropriately substituted anisole XXIX. The amine XXIX is converted into the sulfonamide XXX by a two-step procedure involving sulfonylation using a sulfonylating agent such as p-toluenesulfonyl chloride in the presence of a base such as pyridine, followed by alkylation with an appropriate aryl halomethyl ketone such as a bromomethyl aryl ketone in the presence of a base such as $Cs_2CO_3$ in an organic solvent such as acetone. The cyclization of the sulfonamide XXX to provide XXXI is achieved by heating in an acid such as trifluoroacetic acid. The demethylation of isoquinoline XXXI is achieved under acidic conditions, such as heating with pyridine hydrochloride, leading to XXXII. The phenol XXXII is then converted into the iodide XXXIII by procedures similar to those described for the sequence XV-XVII-XX-XXI in Schemes 4 and 5. Coupling of the iodide XXXIII and the appropriate thiophenol of the general structure VII (Scheme 10) in an organic solvent such as butanol in the presence of a base such as potassium t-butoxide and a catalyst such as $(Ph_3P)_4Pd$ provides compounds of Formula 1L of the present invention.

Scheme 9

The phenols of structure XI can be obtained following the route described in Scheme 9. The protected bromophenol XXXIV can be transformed to the tertiary alcohol XXXV by first a transmetallation using magnesium in an organic solvent such as THF or by using an alkyllithium such as n-butyllithium, followed by addition of the appropriate ketone. Alternatively, fluoroketone XXXVI can be transformed to the corresponding benzyl ether XXXVII by treating with the benzyloxy sodium salt in an organic solvent such as DMF. Treatment of compound XXXVII with alkyl lithium such as methyl lithium or with a Grignard reagent such as methyl magnesium bromide provides compound XXXV. The tertiary alcohol XXXV can be alkylated to XXXIII with an alkyl halide such as methyl iodide in the presence of base such as potassium hydride in an organic solvent such as DMF. Removal of the protecting group by treating XXXV with hydrogen in the presence of a catalyst such as Pd/C (P=Bn or 3,4-DMB) or by using a fluoride source such as tetrabutylammonium fluoride in an organic solvent such as THF (P=TBDMS or TBDPS) provides the phenols of structure XI.

Scheme 10

The thiophenols of the general Formula VII can be obtained using a multi-step sequence shown in Scheme 10. The bromofluorobenzene XXXIX can be first transmetallated with magnesium in an organic solvent such as THF followed by the addition of the appropriate ketone to obtain the corresponding tertiary alcohol of the general Formula XL. The introduction of the thiol function can be effected by treating the fluoro derivatives XL with a thiol source such as trimethylsilylethane thiol in the presence of an hydride such as sodium hydride in an aprotic solvent such as DMF. The resulting Compound XLI can be converted to the thiol VII by treatment with a fluoride source such as tetrabutylammonium fluoride in an organic solvent such as THF. Alternatively, thiol VII can be obtained by treating the fluoroketone XXXVII with sodium methylthiolate giving XLIII and followed by treating XLIII with the appropriate Grignard reagent. Then cleavage of the methylthio ether group can be effected by first oxidizing the sulfur to the sulfoxide using an oxidizing reagent such as mCPB A and then by treating it with trifluoroacetic anhydride. Compounds of Formula VII ($R^3$=lower alkyl) can be obtained by treating a compound of Formula XLI or XLIV with an alkyl halide such as alkyl iodide and a base such as potassium hydride, to provide compounds of Formula XLII or XLV, respectively; conversion of XLII and XLV into VII ($R^3$=lower alkyl) may be effected using methods discussed above.

Scheme 11

Compounds of Formula XVI (Z=CH) can be obtained according to the reaction sequence depicted in Scheme 11. Protection of the bromo alcohol XLVI with a silylating agent such as tertbutyldimethylsilyl chloride in the presence of a base such as triethylamine in an organic solvent such as dichloromethane give compounds XLVII. The formation of the corresponding tertiary alcohols XLVIII can be effected following the same protocol as described for the preparation of compounds XXXV in Scheme 9 followed by treatment with a fluoride source such as tetrabutylammonium fluoride in an organic solvent such as THF to provide compounds XVI (Z=CH).

Scheme 12

The corresponding pyridine alcohol XVI (Z=N) can be synthesized using 2,6-dibromopyridine as starting material. First a transmetallation with an alkyllithium such as butyllithium in an organic solvent such as THF followed by addition of dry ice gives Compound L. Reduction of the acid function by treating the acid L with a chloroformate agent such as ethylchloroformate in a protic solvent such as ethanol followed by a treatment with an hydride source such as lithium aluminum hydride or sodium borohydride gives the corresponding alcohol LI. Compounds XVI (Z=N) can be obtained following the same sequence as described for the transformation of XLVI to XVI (Z=CH) in Scheme 11.

Scheme 13

The bromopyridines of the general Formula XIV can be obtained starting with 2,6-dibromopyridine and using the same protocol as described for the transformation of Compound XXXIV to XXXV in Scheme 9.

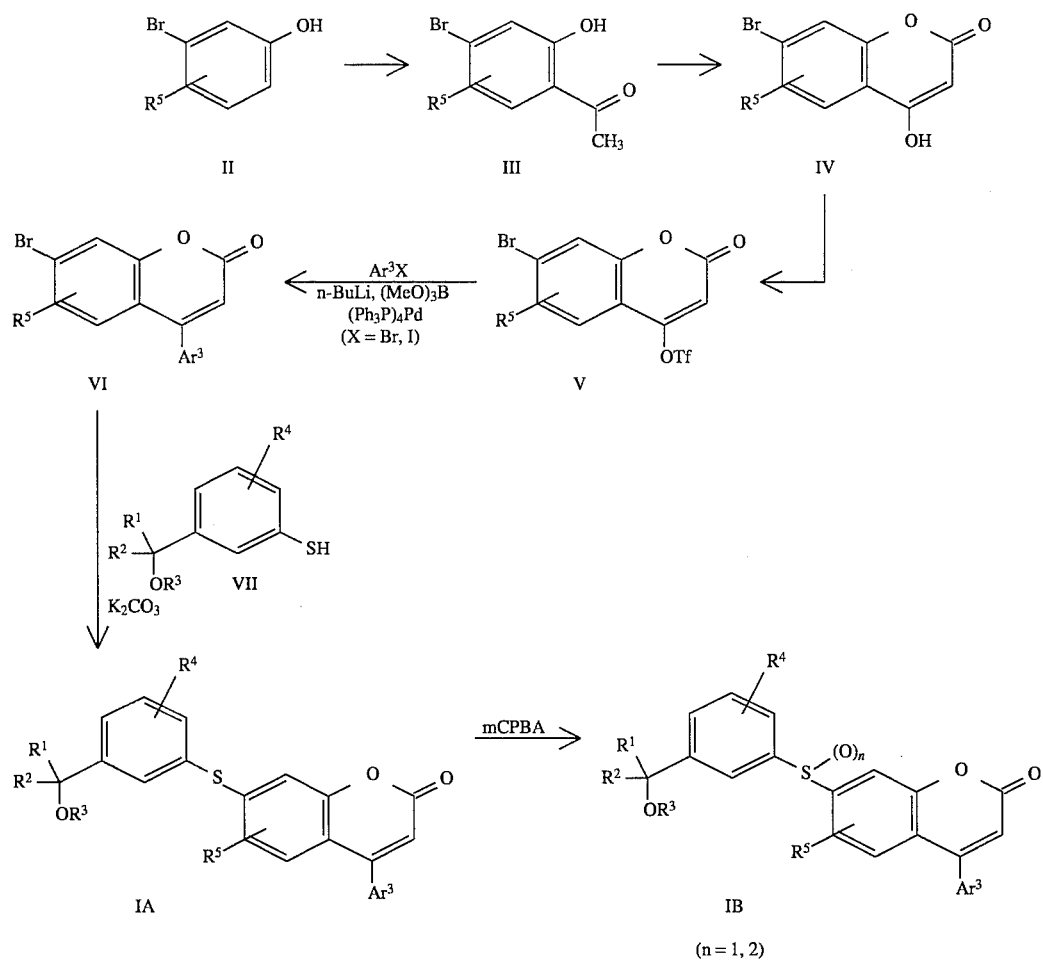
SCHEME 1
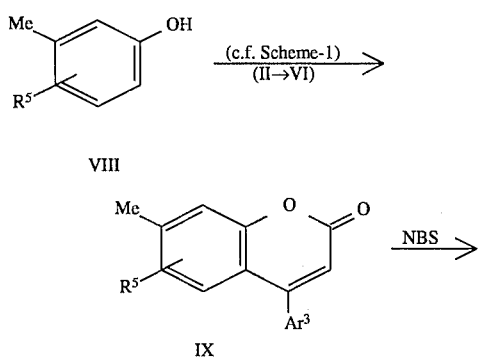
SCHEME 2

-continued
SCHEME 2
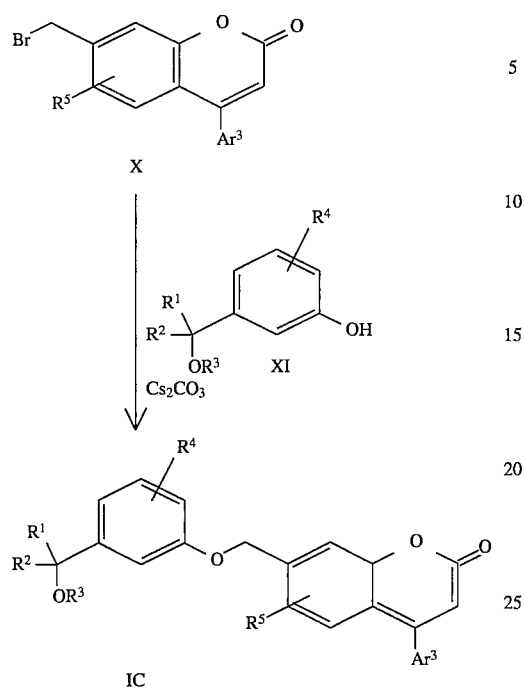
SCHEME 3
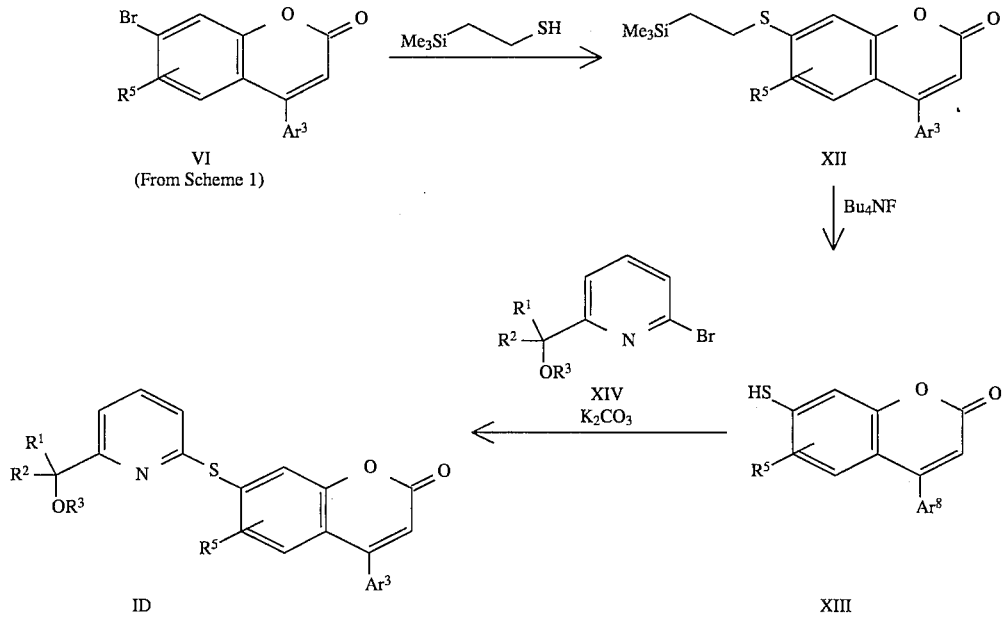

SCHEME 4
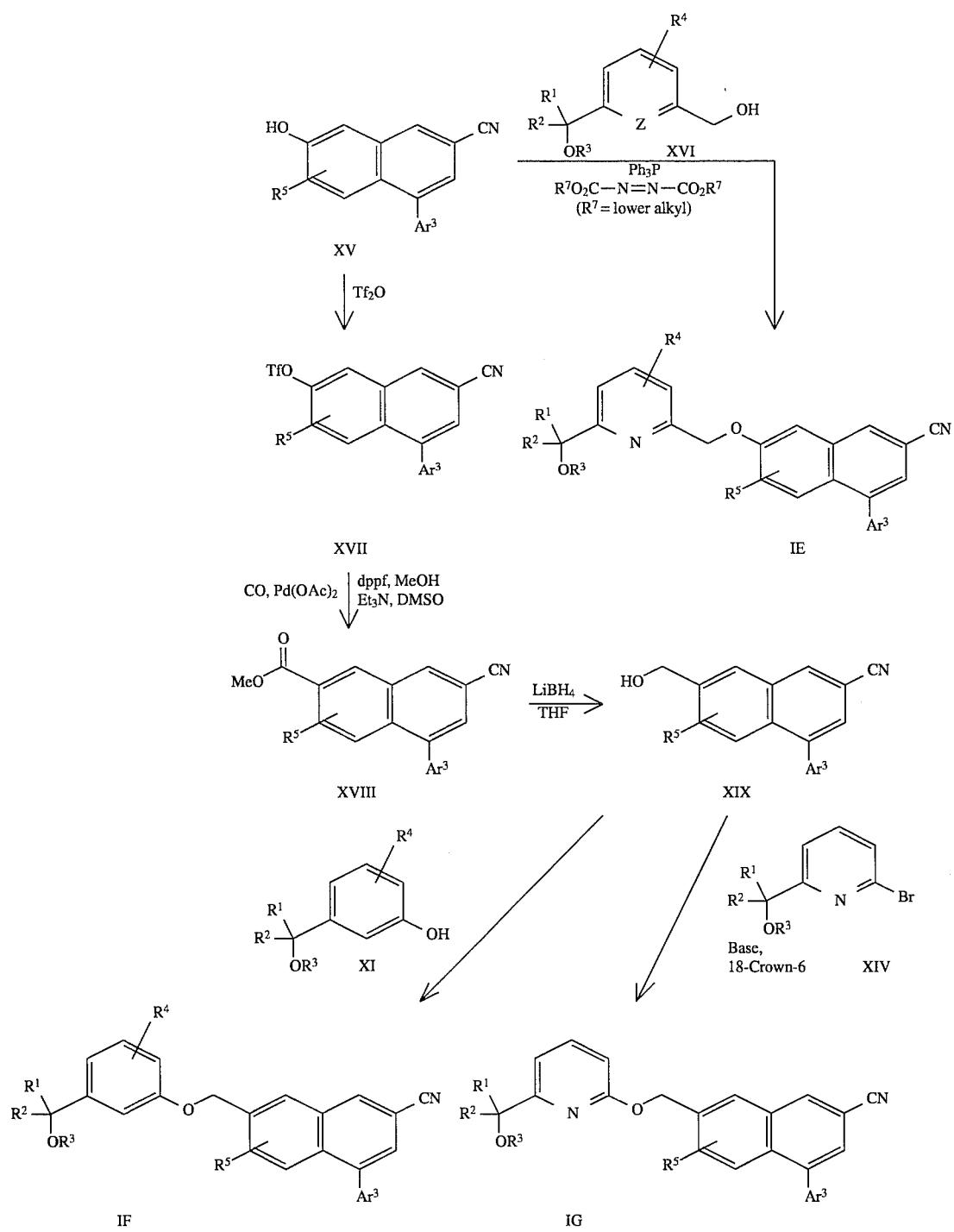

SCHEME 5
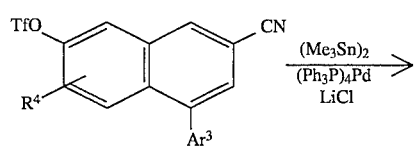
XVII
(From Scheme 4)
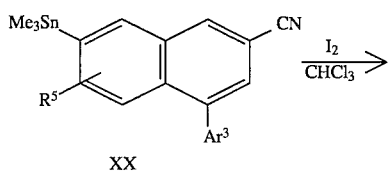
XX
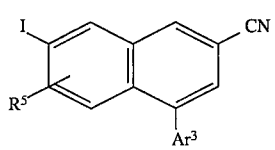
XXI
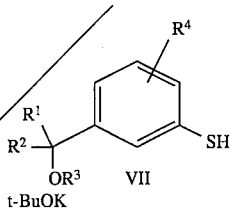
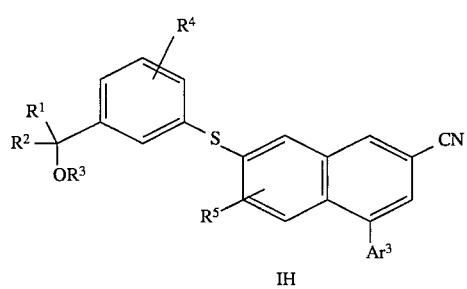
IH
SCHEME 6
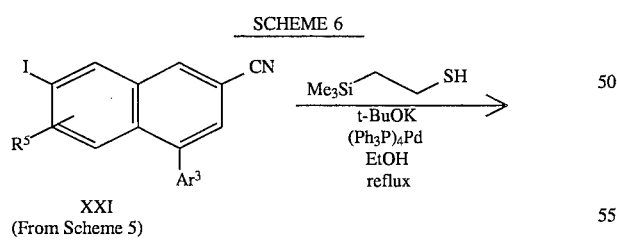
XXI
(From Scheme 5)
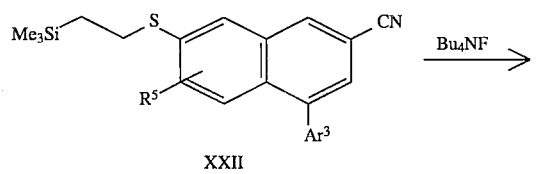
XXII
-continued
SCHEME 6
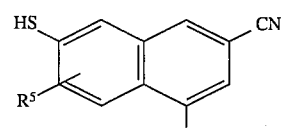
XXIII
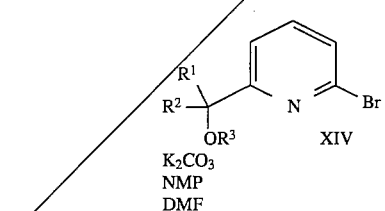
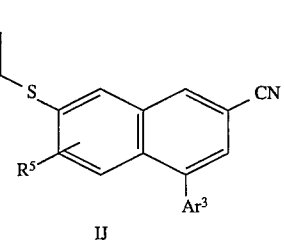
IJ

SCHEME 7
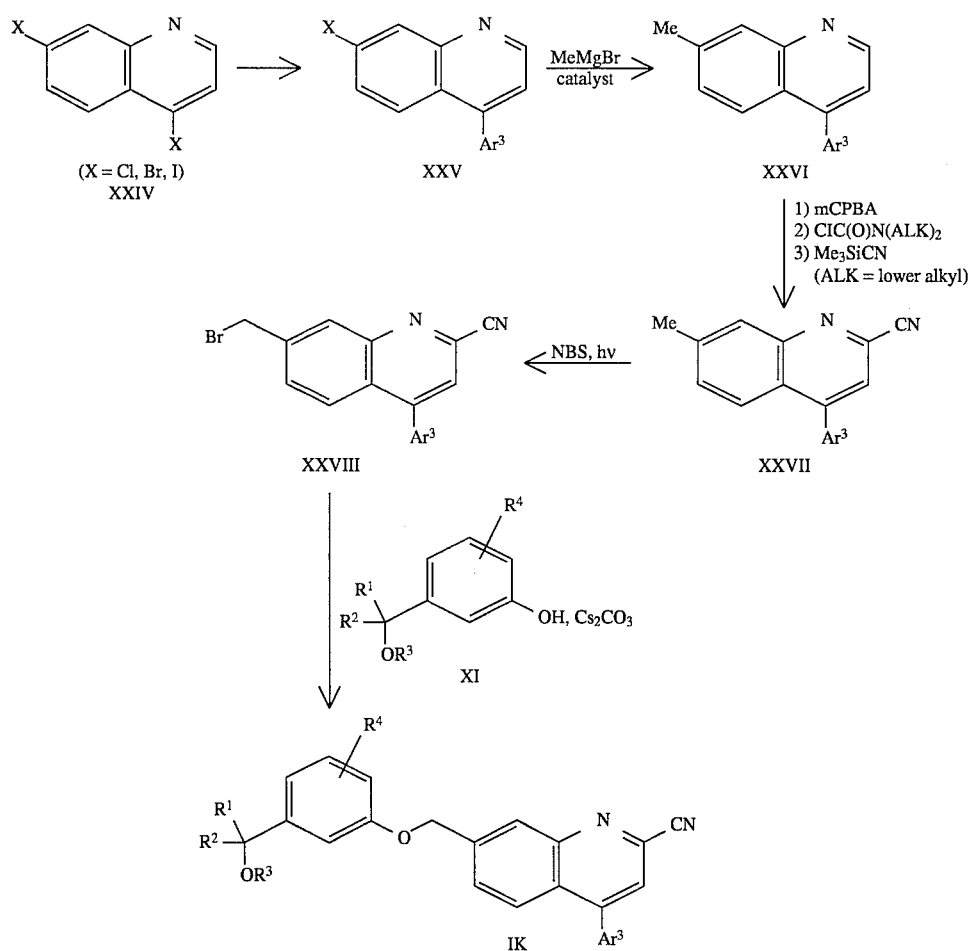
SCHEME 8
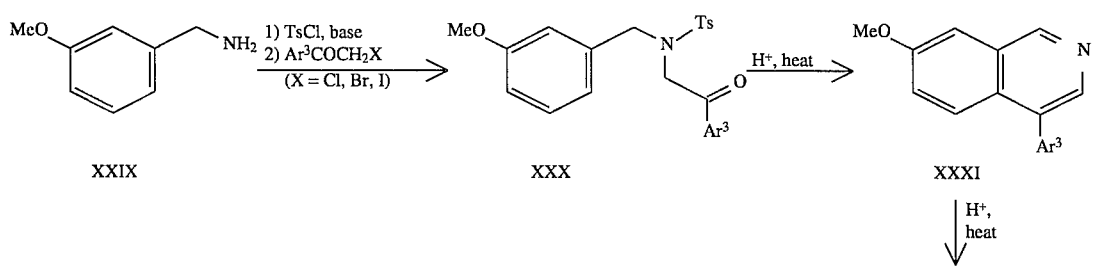

-continued
SCHEME 8
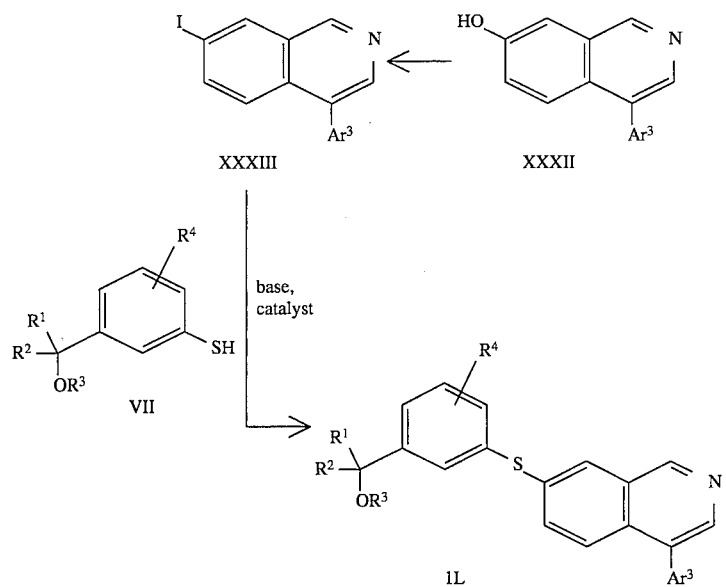
SCHEME 9
PREPARATION OF PHENOLS
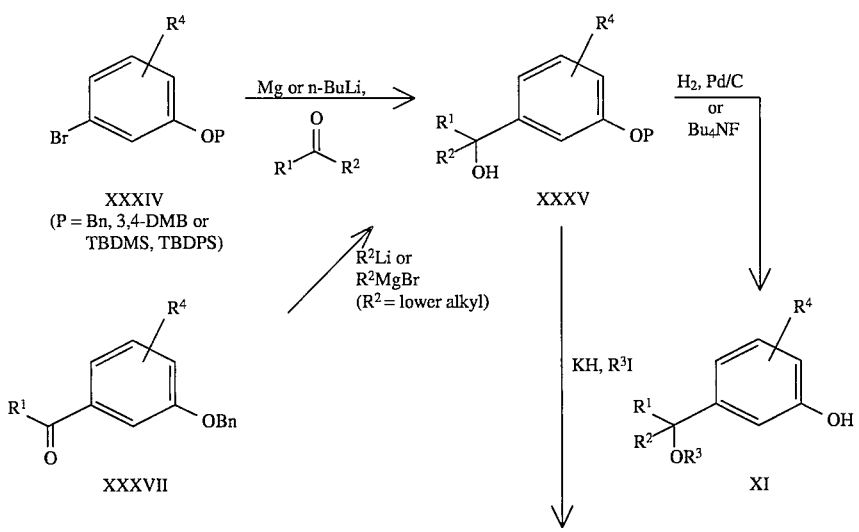

-continued
SCHEME 9
PREPARATION OF PHENOLS
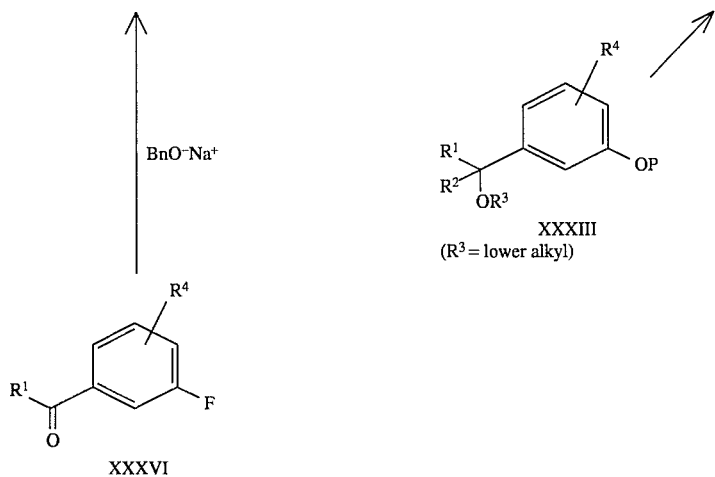
SCHEME 10
PREPARATION OF THIOPHENOLS
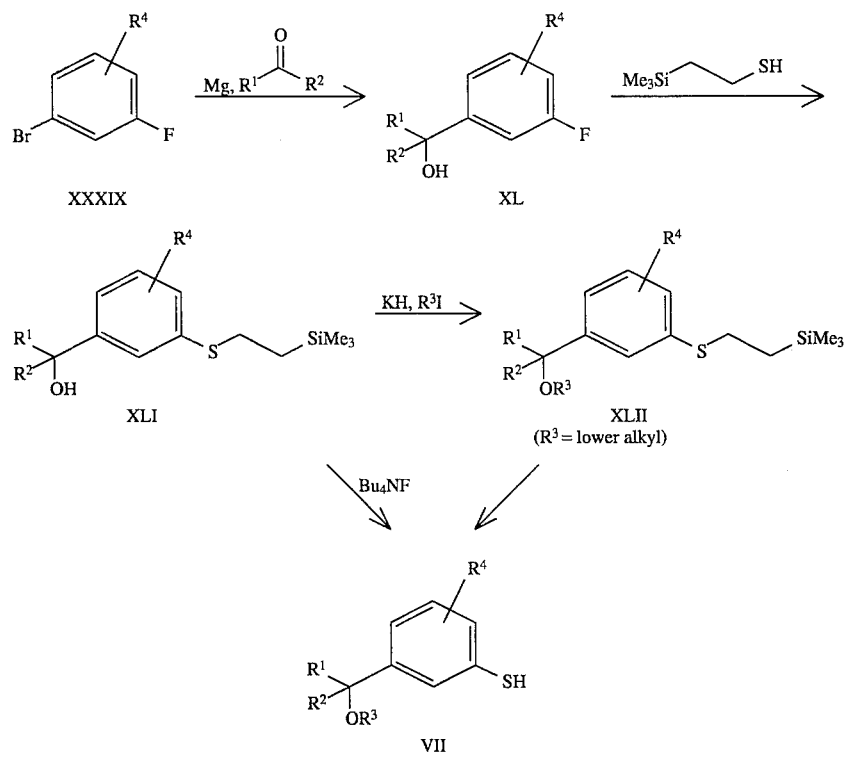

SCHEME 10
PREPARATION OF THIOPHENOLS
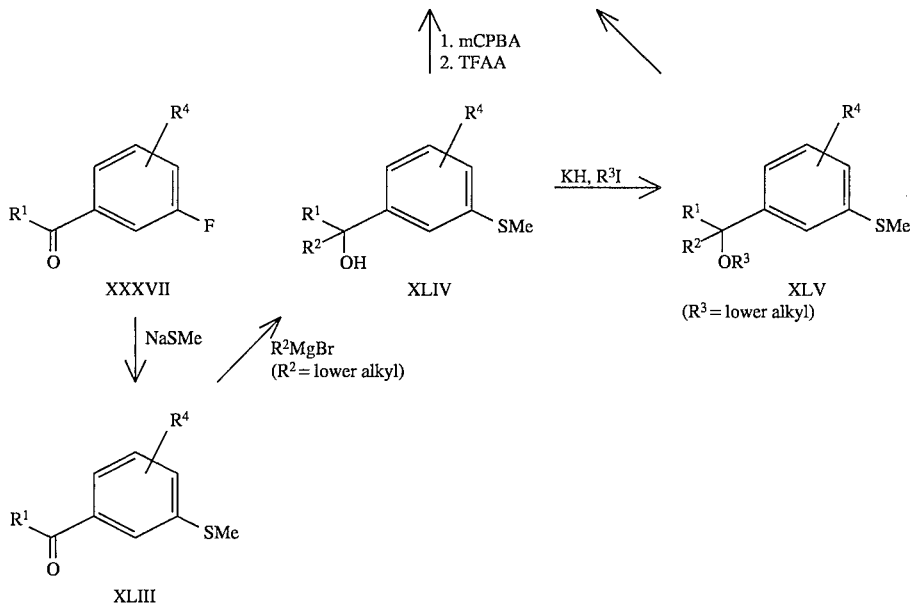
SCHEME 11
PREPARATION OF ALCOHOLS
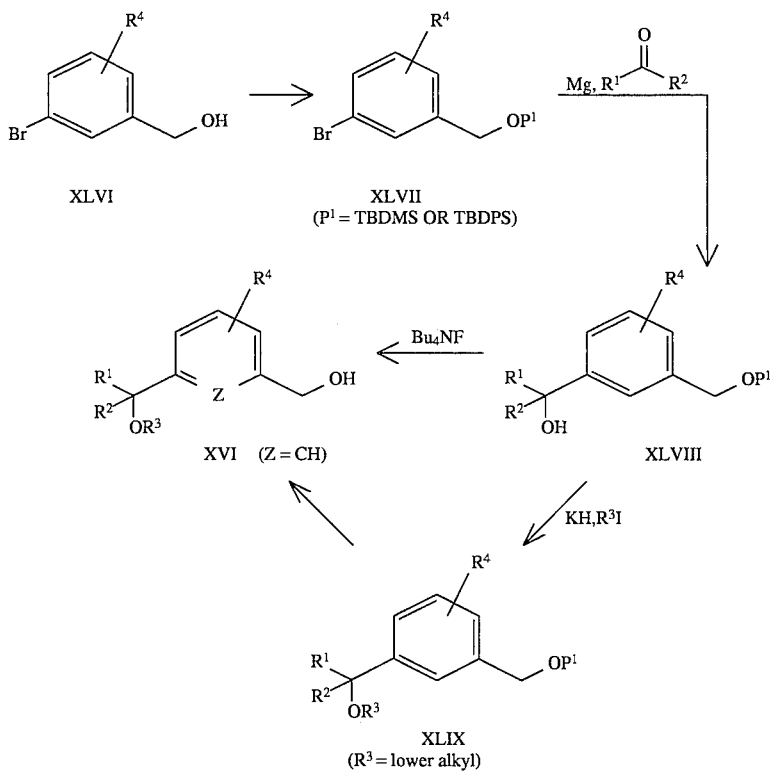

SCHEME 12
PREPARATIONS OF ALCOHOLS

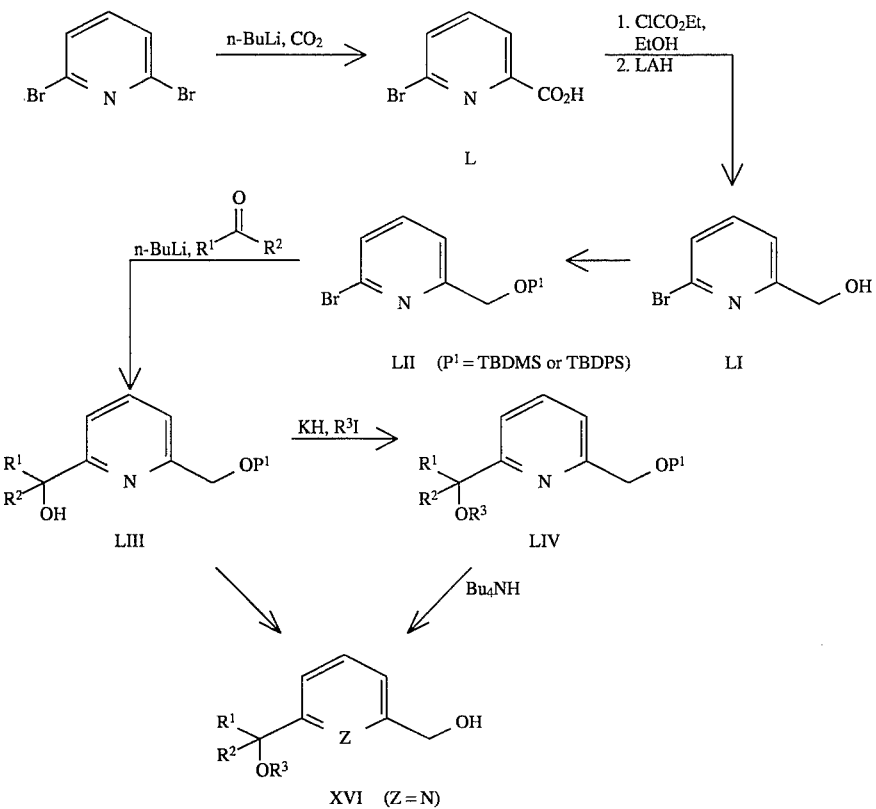

Representative Compounds

Table I illustrates compounds of Formula Ia, which are representative of the present invention.

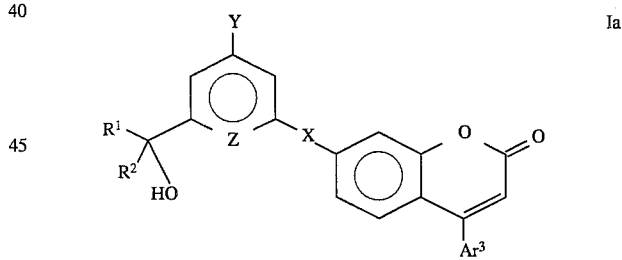

Ia

SCHEME 13
PREPARATION OF BROMOPYRIDINES

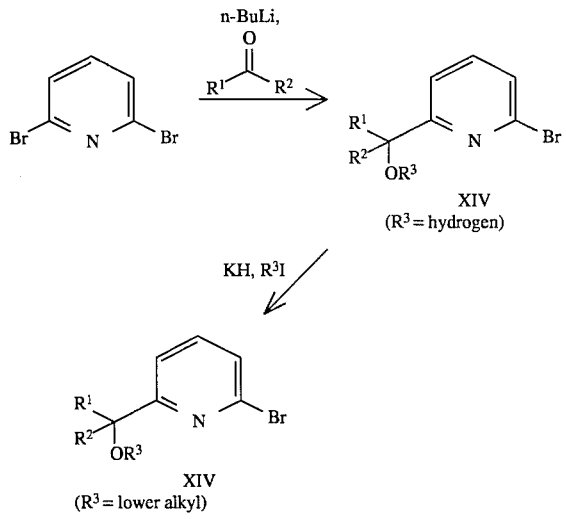

TABLE I

| EX. | $R^1$ | $R^2$ | Z | Y | X | $Ar^3$ |
|---|---|---|---|---|---|---|
| 1 | Et | Et | CH | F | $OCH_2$ | 3-Fu |
| 2 | Et | Et | CH | F | S | 3-Fu |
| 3 | $CF_3$ | $CF_3$ | CH | F | S | 3-Fu |
| 4 | $CF_3$ | $CF_3$ | CH | F | S | 4-F—Ph |
| 5 | $CF_3$ | $CF_3$ | CH | F | S | 3-Py |
| 6 | $CF_3$ | $CF_3$ | CH | F | S | 5-Tz |
| 7 | $CF_3$ | $CF_3$ | CH | F | S | 4-Tz |
| 8 | $CF_3$ | $CF_3$ | CH | F | S | 4-Py |
| 9 | $CF_3$ | $CF_3$ | CH | F | $OCH_2$ | 4-F—Ph |
| 10 | $CF_3$ | $CF_3$ | N | H | S | 3-Fu |
| 11 | n-Bu | H | CH | F | $OCH_2$ | 4-F—Ph |
| 12 | $CF_3$ | $CF_3$ | CH | F | $S(O)_2$ | 4-F—Ph |
| 13 | $CF_3$ | $CF_3$ | CH | F | S(O) | 4-F—Ph |
| 14 | $CF_3$ | $CF_3$ | CH | F | S | 4-Cl—Ph |
| 15 | $CF_3$ | $CF_3$ | CH | F | S | 2,4-Cl—Ph |
| 16 | $CF_3$ | $CF_3$ | N | H | S | 4-F—Ph |

TABLE I-continued

| EX. | R¹ | R² | Z | Y | X | Ar³ |
|---|---|---|---|---|---|---|
| 17 | CF₃ | CF₃ | CH | F | S | 2-Py |
| 18 | CF₃ | CF₃ | CH | F | S | 3-N—MePyr |
| 19 | CF₃ | CF₃ | CH | F | S | Ph |
| 20 | CF₃ | CF₃ | CH | F | S | 1-Im |
| 21 | Ph | CF₃ | CH | F | S | 3-Fu |
| 22 | 2-Tz | CF₃ | CH | F | S | 4-F—Ph |
| 23 | Ph | Et | CH | F | S | 3-Fu |
| 24 | 2-Tz | Me | CH | F | S | 3-Fu |
| 25 | 2-Tz | iPr | CH | F | S | 3-Fu |
| 26 | 2-Im | Et | CH | F | OCH₂ | 3-Fu |
| 27 | 2-Py | Et | CH | H | OCH₂ | 3-Fu |
| 28 | 2-Tz | Et | CH | F | OCH₂ | 3-Th |
| 29 | 2-Tz | Et | CH | F | OCH₂ | 3-Fu |
| 30 | 2-Tz | Et | CH | F | OCH₂ | 4-F—Ph |
| 31 | 2-Tz | Et | CH | F | S(O)₂ | 3-Fu |
| 32 | 2-Tz | Et | CH | F | S | 3-(5-Cl—Th) |
| 33 | 2-Tz | Et | CH | F | S | 3-Th |
| 34 | 2-Tz | Et | CH | F | S | Ph |
| 35 | 2-Tz | Et | CH | F | S | 3-Fu |
| 36 | 2-Tz | Et | CH | F | S | 4-F—Ph |
| 37 | 2-Tz | Et | CH | H | OCH₂ | 3-Fu |
| 38 | 2-Tz | Et | CH | H | OCH₂ | 3-Th |
| 39 | CF₃ | CF₃ | CH | F | S | 3-NO₂—Ph |
| 40 | CF₃ | CF₃ | CH | F | S | 3-Cl,4-F—Ph |
| 41 | CF₃CF₂ | CF₃CF₂ | CH | F | S | 4-F—Ph |
| 42 | CF₃ | CF₃ | CH | F | S | CF₃ |
| 43 | CF₃ | CF₃ | CH | F | S | 3-CF₃O—Ph |

Table II illustrates compounds of Formula Ib which are further representative of the present invention.

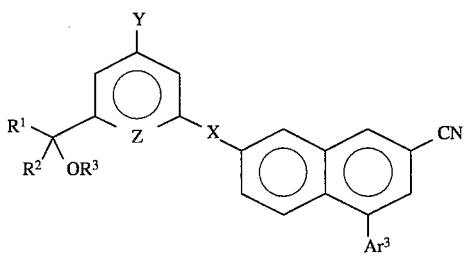

Ib

TABLE II

| EX. | R¹ | R² | R³ | Z | Y | X | Ar³ |
|---|---|---|---|---|---|---|---|
| 46 | Et | Et | H | N | H | CH₂O | 3-Fu |
| 47 | Et | Et | H | CH | F | OCH₂ | 3-Fu |
| 48 | Et | Et | H | N | H | S | 3-Fu |
| 49 | CF₃ | CF₃ | H | N | H | CH₂O | 3-Fu |
| 50 | CF₃ | CF₃ | H | N | H | CH₂O | Ph |
| 51 | CF₃ | CF₃ | H | N | H | S | 3-Fu |
| 52 | 2-Tz | Et | H | N | H | S | 3-Fu |
| 53 | 2-Tz | Et | H | CH | F | S | 3-Fu |
| 54 | 2-Tz | Et | H | N | H | OCH₂ | 3-Fu |
| 55 | 2-Tz | Et | H | N | H | CH₂O | 3-Fu |
| 56 | 2-Tz | Et | Me | N | H | CH₂O | 3-Fu |
| 57 | 2-Tz | Et | H | CH | H | OCH₂ | 3-Fu |
| 58 | 2-Tz | Et | Me | CH | H | OCH₂ | 3-Fu |
| 59 | 2-Tz | Et | H | CH | H | CH₂O | 3-Fu |

Table III illustrates compounds of Formula Ic which are further representatives of the present invention.

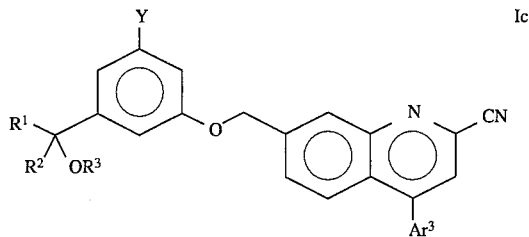

Ic

TABLE III

| Ex | R¹ | R² | R³ | Y | Ar³ |
|---|---|---|---|---|---|
| 60 | Me | Me | H | H | 3-Fu |
| 61 | Et | Et | H | H | 3-Fu |
| 62 | H | H | H | H | 3-Fu |
| 63 | Et | iPr | H | H | 3-Fu |
| 64 | CF₃ | CF₃ | Me | F | 3-Fu |
| 65 | t-Bu | Et | H | H | 3-Fu |
| 66 | Et | Et | H | F | 3-Fu |
| 67 | CF₃ | CF₃ | H | F | 3-Fu |
| 68 | CF₃ | CF₃ | H | F | 4-F—Ph |
| 69 | Ph | Ph | H | F | 3-Fu |
| 70 | 2-Py | Et | H | H | 3-Fu |
| 71 | 3-Fu | Et | H | H | 3-Fu |
| 72 | Ph | Et | H | H | 3-Fu |
| 73 | 2-Tz | Et | H | F | 3-Fu |
| 74 | 2-Tz | Et | H | H | 3-Fu |

Table IV illustrates compounds of Formula Id which are representative of the present invention

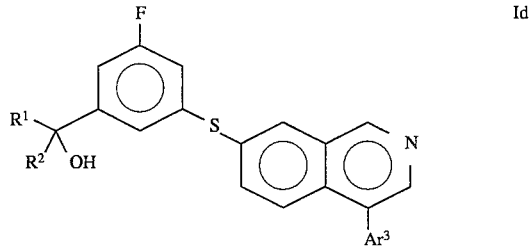

Id

TABLE IV

| Ex | R¹ | R² | Ar³ |
|---|---|---|---|
| 75 | CF₃ | CF₃ | 3-Fu |
| 76 | CF₃ | CF₃ | Ph |
| 77 | 2-Tz | Et | 3-Fu |

Assays For Determining Biological Activity

Compounds of Formula I can be tested using the following assays to determine their mammalian leukotriene biosynthesis inhibiting activity.

Human 5-Lipoxygenase Inhibitor Screen

Objective of the Assay: The objective of the assay is to select agents which specifically inhibit the activity of human 5-lipoxygenase using a 100,000×g supernatant fraction prepared from insect cells infected with recombinant baculovirus containing the coding sequence for human 5-lipoxygenase. Enzyme activity is measured spectrophotometrically from the optimal rate of conjugated diene formation ($A_{234}$) measured after the incubation of the enzyme with arachidonic acid in the presence of ATP, calcium ions and phosphatidylcholine.

Description of Procedure: The activity of 5-lipoxygenase is measured using a spectrophotometric assay and recombinant human 5-lipoxygenase as a source of enzyme. The 100,000×g fraction from S19 cells infected with the recombinant baculovirus rvH5LO(8-1) containing s the coding region sequence for human 5-lipoxygenase is prepared as described by Denis et al., (*J. Biol. Chem.*, 266, 5072–5079 (1991)). The enzymatic activity is measured, using a spectrophotometric assay from the optimal rate of conjugated diene formation ($A_{234}$) using the procedure described by Riendeau et al., (*Biochem. Pharmacol.* 38, 2323–2321, (1989)) with minor modifications. The incubation mixture contains 50 mM sodium phosphate pH 7.4, 0.2 mM ATP, 0.2 mM $CaCl_2$, 20 µM arachidonic acid (5 µL from a 100-fold concentrated solution in ethanol), 12 µg/mL phosphatidylcholine, an aliquot of the 100,000×g fraction (2–10 µL) and inhibitor (0.5 mL final volume). Inhibitors are added as 500-fold concentrated solutions in DMSO. Reactions are initiated by the addition of an aliquot of the enzyme preparation and the rate of conjugated diene formation is followed for 2 min. at r.t.. The reactions are performed in semi-micro cuvettes (0.7 mL capacity, 10 mm path length and 4 mm internal width) and the absorbance changes are recorded with a Hewlett-Packard diode array spectrophotometer (HP 8452A) connected to the ChemStation using UV/VIS Kinetics Software. Enzymatic activity is calculated from the optimal rate of the reaction by a linear fit of the variation of $A^{234}$ during the first twenty seconds using the least square method for the equation $A_{234}=V_o t+A^\circ$ where $V_o$ is the rate, t is the time, and $A_o$ is the absorbance at zero time. The results are expressed as percentages of inhibition of the reaction rate relative to controls (typically between 0.15–0.21 AU/min) containing the DMSO vehicle.

Human Polymorphonuclear (PMN) Leukocyte $LTB_4$ Assay

A. Preparation of Human PMN. Human blood is obtained by antecubital venepuncture from consenting volunteers who have not taken medication within the previous 7 days. The blood is immediately added to 10% (v/v) trisodium citrate (0.13M) or 5% (v/v) sodium heparin (1000 IU/mL). PMNs are isolated from anticoagulated blood by dextran sedimentation of erythrocytes followed by centrifugation through Ficoll-Hypaque (specific gravity 1.077), as described by Boyum (*Scand. J. Clin. Lab. Invest.*, 21 (Supp 97), 77 (1968)). Contaminating erythrocytes are removed by lysis following exposure to ammonium chloride (0.16M) in Tris buffer (pH 7.65), and the PMNs are resuspended at $5\times10^5$ cells/mL in HEPES (15 mM)-buffered Hanks balanced salt solution containing $Ca^{2+}$(1.4 mM) and $Mg^{2+}$(0.7 mM), pH 7.4.

B. Generation and Radioimmunoassay of $LTB_4$. PMNs (0.5 mL; $2.5\times10^5$ cells) are placed in plastic tubes and incubated (37° C., 2 min) with test compounds at the desired concentration or vehicle (DMSO, final concentration 0.2%) as control. The synthesis of $LTB_4$ is initiated by the addition of calcium ionophore $A_{23187}$ (final concentration 10 µM) or vehicle in control samples and allowed to proceed for 5 min. at 37° C. The reactions are then terminated by the addition of cold methanol (0.25 mL) and samples of the entire PMN reaction mixture are removed for radioimmunoassay of $LTB_4$.

Samples (50 µL) of authentic $LTB_4$ of known concentration in radioimmunoassay buffer (RIA) buffer (potassium phosphate 1 mM; disodium EDTA0.1 mM; Thimerosal 0.025 mM; gelatin 0.1%, pH 7.3) or PMN reaction mixture diluted 1:1 with RIA buffer are added to reaction tubes. Thereafter [$^3$H]-$LTB_4$ (10 nCi in 100 µL RIA buffer) and $LTB_4$-antiserum (100 µL of a 1:3000 dilution in RIA buffer) are added and the tubes vortexed. Reactants are allowed to equilibrate by incubation overnight at 4° C. To separate antibody-bound from free $LTB_4$, aliquots (50 µL) of activated charcoal (3% activated charcoal in RIA buffer containing 0.25% Dextran T-70) are added, the tubes vortexed, and allowed to stand at r.t. for 10 min. prior to centrifugation (1500×g; 10 min; 4° C.). The supernatants containing antibody-bound $LTB_4$ are decanted into vials and Aquasol 2 (4 mL) is added. Radioactivity is quantified by liquid scintillation spectrometry. The specificity of the antiserum and the sensitivity of the procedure have been described by Rokach et al., *Prostaglandins Leukotrienes and Medicine*, 13, 21 (1984). The amount of $LTB_4$ produced in test and control samples is calculated. Inhibitory dose-response curves are constructed using a four-parameter algorithm and from these the $IC_{50}$ values are determined.

Human Whole Blood Assay IN VITRO For $LTB_4$ Production

Fresh blood is collected in heparinized tubes by venipuncture from human volunteers. A $^{500}$ µL aliquot is incubated with one of the test compounds at final concentrations varying from 3 nM to 3 mM at 37° C. for 15 min. Drug stock solutions are made up in DMSO and 1 µL of the stock solution is added to each assay tube. The blood is then incubated with $A_{23187}$ (in 5 µL autologous plasma, 25 µM final concentration) at 37° C. for 30 min. At the end of incubation, plasma is obtained (12,000×g, 15 min) and a 100 µL aliquot is added to 400 µL methanol for protein precipitation. The mixture is vortexed, centrifuged and the supernatant stored at −70° C. until assayed for $LTB_4$ by standard RIA.

Pulmonary Mechanics In Trained Conscious Squirrel Monkeys—A Non-Invasive Technique Objective of the Assay: To assess pulmonary mechanics changes in the airways of conscious squirrel monkeys with the use of a double plethysmograph instead of thoracic catheterization of the pleural space as in the former invasive technique to measure airway resistance ($R_1$) and dynamic compliance ($C_{dyn}$). The non-invasive technique measures changes in the pulmonary parameter "specific airway resistance" (sRaw) which is defined as airway resistance×thoracic gas volume. Agonists like $LTD_4$, 50 µg/mL or *Ascaris suum* antigen (1:25 dilution) aerosol challenge cause an increase in sRaw values, i.e. bronchoconstriction, and consequently allow the evaluation of specific antagonists against these agonists.

For evaluation of compounds in this model, monkeys are fasted overnight and dosed the following morning. The compound is dissolved in 1% methocel solution and given orally at doses ranging from 1 to 0.003 mg/kg in a volume of 1 mL/kg in the home cage. Three h later the monkeys are placed in a chair within a thoracic plethysmograph whilst the muzzle of the monkey is placed into a nasal plethysmograph through which he breathes. Baseline values for sRaw (cm $H_2O \times sec$.) are taken and at 4 h post compound administration, the monkeys are challenged with an aerosol of the specific agonist. The aerosol is generated by an ultrasonic DeVilbiss nebulizer and administered to the monkeys in the nasal plethysmograph at a rate of 2 liters/minute with the aid of a Pulmo-Aide pump (DeVilbiss, 561 series) for 10 min. For data collection, a Buxco Electronics Inc. respiratory computer is utilized which facilitates continuous recording of pulmonary function changes and derives a value for sRaw for each animal.

Following challenge, each minute of data is calculated as a percent change from control values for specific airway resistance (sRaw). The results for each test compound are subsequently obtained for a minimum period of 60 minutes post challenge which are then compared to previously obtained historical baseline control values for that monkey. In addition, the overall values for 60 minutes post-challenge for each monkey (historical baseline values and test values) are averaged separately and are used to calculate the overall percent inhibition of $LTD_4$ or Ascaris antigen response by the test compound. For statistical analysis, paired t-test is used (Reference: Pennock, B. E. et al., *J. Appl. Physiol.: Respirat. Environ. Exercise Physiol.* 46 (2) 399–406, 1979.

DOG MODEL:

Whole Blood (ex vivo) $LTB_4$ and Urinary $LTE_4$ Excretion Assays

Normal male dogs are anaesthetised, bronchially intubated and catheterised for drug administration and urine collection. After the first urine voiding (15 min.), blood is collected into anticoagulant to define the baseline $LTB_4$ biosynthetic capacity of whole dog blood, and to determine the in vitro potency of this compound in dog blood. Compounds are dissolved in PEG 200/$H_2O$ to a concentration of 0.3 mg/mL. In tubes #1–4, 10 μL of PEG 200 (vehicle) is added to serve as controls. Compounds are titrated from 0.0015 μM–0.37 μM (final concentration). Compounds are added in a volume of 10 μL in ascending concentrations in duplicate (tubes #5–16). The highest drug concentration is also added to tube #17 as a drug blank. To each tube, 500 μL venous blood is added, followed by incubation for 15 minutes at room temperature, without shaking. Tubes #1 & 17, then receives 5 μL of autologous plasma containing 10% DMSO (blanks). 5 μL of autologous plasma containing 10% DMSO and 5 mM A23187 (final 50 μM) are added to tubes #2 to 16 to stimulate $LTB_4$ synthesis. Samples are incubated for 30 min. at 37° C., and the reaction terminated by centrifugation. Aliquots of plasma is added to 4 volumes of MeOH, and centrifuged to precipitate proteins prior to analysis of $LTB_4$ content by RIA.

A bolus dose of compounds (0.1, 0.05 or 0.025 mg/kg in PEG200/$H_2O$) is then administered intravenously, followed by a continuous infusion (via a 21 gauge IV catheter) of the compounds (2.5, 0.8 or 0.25 μg/kg/min). Urine is continuously collected for 1 hour intervals. Sample volumes are recorded, and urinary $LTE_4$ stabilised with 10N NaOH solution (10 μL/mL), prior to freezing (−70° C.). Venous blood is similarly collected (into anticoagulant) contralateral to the IV at hourly intervals. All blood samples are immediately aliquoted (500 μL). To one aliquot, 5 μL of autologous plasma containing 10% DMSO is added as a blank. To other aliquots, 5 μL of autologous plasma containing 10% DMSO and 5 mM $A_{23187}$ is added (final 50 μM) to stimulate $LTB_4$ synthesis as described above.

Aliquots (10 mL) of thawed urine are centfifuged (10,000×g), and the supernatant adjusted to pH 5.4 with 100 μL glacial acetic acid. As a recovery standard, 3 nCi of [14,15,19,20-$^3$H]-$LTC_4$ (12 pg) is added. Samples are applied to a 3 gm particle $C_{18}$ precolumn, and washed with 2 volumes of 0.1% $NH_4OAc$ buffer pH 5.4. Peptide leukotrienes are then eluted onto a $C_{18}$ analytical HPLC column, and separated with a 66% MeOH/34% 0.1% $NH_4Ac$ pH 5.4 (v/v) mobile phase containing 1 mM EDTA. Fractions eluting with the retention time of synthetic $LTC_4$ (obtained from daily calibration with standards) are collected for estimation of [$^3$H]-$LTC_4$ recovery by scintillation counting. Prior experiments established that recoveries of [$^3$H]-$LTC_4$ and [$^3$H]-$LTE_4$ from dog urine after RP-HPLC are comparable (86.8±1.9% and 83.1±6.1% respectively). In some experiments synthetic $LTE_4$ (0.5 ng/mL) and/or 0.1 nCi [$^3$H]-$LTE_4$ (0.4 pg) are added to certain samples to identify the exact retention time of $LTE_4$. Fractions (0.75 min, 0.75 mL) eluting before, during and after the predicted retention time of synthetic $LTE_4$ (from daily calibration) are collected into sequential wells in a polypropylene microtitre plate, aliquots (200 μL) are removed to identify the retention time of added [$^3$H]-$LTE_4$), and the remainder frozen to −70° C. and lyophilised in a vacuum centrifuge. Fractions are redissolved in 50 μL of 20 mM $Na_2PO_4$ pH 7.2 containing 0.9% NaCl, 0.02% sodium azide, 0.1 mM phenyl methyl sulphonyl fluoride and 1% gelatin and mixed with 2–3 nCi of [14,15,19,20-$^3$H]-$LTE_4$ (5.2–7.8 pg) and an anti-$LTC_4$ mouse monoclonal antibody (21% cross-reactivity with $LTE_4$; final dilution 1/150,000) and incubated for 2 h at 21° C. Free ligand is precipitated by addition of dextran coated charcoal and centrifugation. An aliquot of the supernatant is removed and the concentration of $LTE_4$ immunoactive material estimated by comparison of the unknown bound [$^3$H]-$LTE_4$ against a standard curve derived by serial dilution of a synthetic $LTE_4$ stock solution (4000–7.8 pg/tube). $LTE_4$ concentration is calculated as the immunoreactive material (pg) in n co-eluting fractions—n×average background immunoreactive material (pg) in pre- and post-$LTE_4$ fractions, corrected for [$^3$H]-$LTC_4$ recovery, and the fraction volume removed for estimating the retention time of added [$^3$H]-$LTE_4$. Urinary $LTE_4$ excretion (ng/hour) is then calculated from the concentration and excretion volume, and related to values obtained during the first collection on a case by case basis. % inhibition of baseline $LTE_4$ is calculated for the 5–6 and 6–7 h time points, and the mean value obtained for the treatment group. An $ED_{50}$ is then calculated using these values and the infusion dose by non-linear regression analysis (4 parameter fit).

Aliquots (50 μL) of MeOH supernatants of plasma are similarly diluted into 50 μL of the above RIA buffer and mixed with 5–8 nCi of [5,6,8,9,11,12,14,15-$^3$H]-$LTB_4$ (1.7–2.7 pg) and an anti-$LTB_4$ sheep antiserum (final dilution 1/7500). $LTB_4$ is quantified as above against a standard curve derived by serial dilution of a synthetic $LTB_4$ stock solution (1000–1.95 pg/tube). $LTB_4$ generation stimulated by 50 μM $A_{23187}$ is derived by subtraction of the blank value (DMSO alone) and values are related to those obtained in the first (pre-treatment) sample. An $ED_{50}$ is then calculated using the maximum values for ex vivo inhibition, and the infusion dose, by non-linear regression analysis. For the calculation of in vitro $IC_{50}$ values, blank values for $LTB_4$ production are subtracted from each subsequent value, and the % inhibition calculated for each drug concentration (compared with PEG/$H_2O$). The $IC_{50}$ is then calculated by non-linear regression analysis.

The invention will now be illustrated by the following non-limiting examples in which, unless stated otherwise:

(i) all operations were carded out at room or ambient temperature, that is, at a temperature in the range 18°–25° C., (ii) evaporation of solvent was carded out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; q. quartet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliter(s)), gL (microliter(s)), g (gram(s)), mg (milligrams(s)), mol (mole(s)), mmol (millimole(s)), eq (equivalent(s)).

PREPARATION OF PHENOLS

PHENOL 1:

5-Fluoro-3-[1-hydroxy-1-(thiazol-2-yl)propyl]phenol

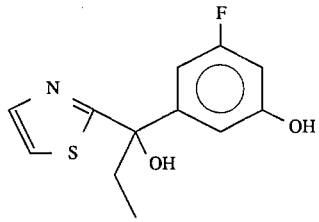

Step 1:

1-(Thiazol-2-yl)propanone

To a solution of thiazole (10 g, 0.12 mol) in dry THF (100 mL) at −78° C. was added BuLi (50 mL, 2.47M in hexane). The resulting reaction mixture was stirred 30 min. then ethyl propionate (18.8 mL, 0.16 mol) in THF was added and the cooling bath was removed. After 30 min. an aqueous solution of $NH_4OAc$ (25%) was added and the THF evaporated. Ether was added and washed successively with $H_2O$, brine, dried over $MgSO_4$ and evaporated. The residue was distilled under vacuum to give 12.1 g (73%) of the title compound.

Step 2:

5-Fluoro-3-[1-hydroxy-1-(thiazol-2-yl)prop yl](O-benzyl)phenol

A solution of 3-benzyloxy-1-bromo-5-fluorobenzene (EP: 0385662, ICI, Pharma) (5.4 g, 19.4 mmol) in dry THF (30 mL) containing magnesium (941 mg, 38.7 mmol) was heated until the Grignard reagent was formed then the reaction mixture was stirred at r.t. for 30 min. and transferred to a solution of 1-(thiazol-2-yl)propanone in dry THF at 0° C. The reaction mixture was stirred for 30 min. then an aqueous solution of $NH_4OAc$ (25%) was added and the THF evaporated. The residue was diluted with EtOAc and washed successively with $H_2O$, brine, dried over $MgSO_4$ and evaporated. The residue was purified by chromatography using hexane:EtOAc 9:1 to give 2.2 g, (50%) of the title product.

Step 3:

5-Fluoro-3-[1-hydroxy-1-(thiazol-2-yl)propyl]phenol

To a solution of 5-fluoro-3-[1-hydroxy-1-(thiazol-2 -yl) propyl](O-benzyl)phenol (200 mg, 0.58 mmol) in MeOH (9 mL) was added 10% Pd on charcoal (200 mg) and ammonium formate (180 mg, 2.9 mmol). The reaction mixture was refluxed for 2 h and then flitrated through a pad of celite and washed with EtOAc. After evaporation of the solvent, the residue was purified by chromatography on silica gel using a mixture of hexane:EtOAc 7:3 to give 116 mg (79%) of the title compound.

$^1H$ NMR (400 MHz, $CDCl_3$); δ0.89 (t, 3H); 2.32 (m, 2H); 3.44 (s, 1H); 5.59 (s, 1H); 6.42 (dd, 1H); 6.83 (m, 2H); 7.28 (d, 1H); 7.69 (d, 1H).

PHENOL 2:

5-Fluoro-3-(3-hydroxypent-3-yl)phenol

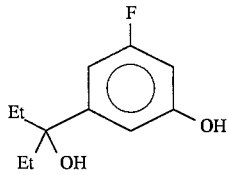

Step 1:

1-Bromo-3-(3,4-dimethoxybenzyloxy)-5-fluorobenzene

Sodium hydride (80% disp. in oil; 933 mg, 31.1 mmol) was added, all at once, to 3,4-dimethoxybenzyl alcohol (3.48 g, 20.7 mmol) in DMF (40 mL) at 0° C. and under Ar. After 5 min., the mixture was allowed to warm to r.t. After 1 h, 1-bromo-3,5-difluorobenzene (4 g, 20.7 mmol) in DMF (5 mL) was added dropwise at r.t. The resulting mixture was kept at this temperature for 16 h and slowly poured into $H_2O$ (500 mL). It was extracted with EtOAc (3×) and the combined organics were washed with 25% $NH_4OAc$ buffer (1×), $H_2O$ (2×) and brine. The solution was dried ($MgSO_4$) and concentrated to give a pale yellow solid that was purified by column chromatography on silica gel (EtOAc:hexane, 10:90–15:85) to afford the title compound as a white solid (5.85 g, 83%).

Step 2:

5-Fluoro-3-(3-hydroxypent-3-yl)[O-(3,4-dimethoxybenzyl)]phenol

To a solution of 1-bromo-3-(3,4-dimethoxybenzyloxy)-5-fluorobenzene (Step 1) (1.02 g) in THF (10 mL) at −78° C. was added n-BuLi (1.5 mL of a 2.2M solution) dropwise. After 30 min. 3-pentanone (0.33 mL) was added and after 30 min. the bath was removed and the mixture stirred for 10 min. The reaction mixture was quenched with NH$_4$OAc buffer and extracted with EtOAc. The organics were dried (MgSO$_4$) and concentrated. Chromatography of the residue (silica gel; hexane/EtOAc (3:1) provided the title compound as a colorless oil.

Step 3:

5-Fluoro-3-(3-hydroxypent-3yl)phenol

Following the procedure described for Phenol 1, Step 3, but substituting 5-fluoro-3-(3-hydroxypent-3-yl)[O-(3,4-dimethoxybenzyl)]phenol from Step 2 for 5-fluoro-3-[1-hydroxy-1-(thiazol-2 -yl)propyl](O-benzyl)phenol the title compound was obtained as a solid.

$^1$H NMR (300 MHz, Acetone-d$_6$); δ0.72 (t, 6H); 1.78 (m, 4H); 3.61 (s, 1H); 6.41 (dd, 1H); 6.67 (dd, 1H); 6.76 (s, 1H); 8.50 (s, 1H).

PHENOL 3:

5-Fluoro-3-(hexafluoro-2-hydroxyprop-2-yl)phenol

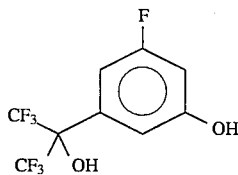

Following the procedure described for Phenol 2, Step 2, and Phenol 1, Step 3, but substituting hexafluoroacetone (Aldrich) for 3 -pentanone, the title compound was obtained.

$^1$H NMR (300 MHz, Acetone-d$_6$); δ6.75 (dd, 1H); 7.0 (d, 1H); 7.12 (s, 1H); 8.2 (s, 1H).

PHENOL 4:

3-Diphenylhydroxymethyl-5-fluorophenol

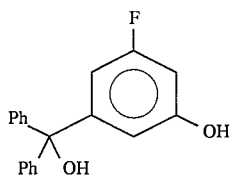

Following the procedure described for Phenol 2, Step 2 and the procedure described for Phenol 1, Step 3 but substituting benzophenone for 3-pentanone, the title compound was obtained.

$^1$H NMR (300 MHz, Acetone-d$_6$); δ5.34 (s, 1H); 6.48 (m, 1H); 6.55–6.60 (m, 2H); 7.23–7.35 (m, 10H); 8.64 (s, 1H).

PHENOL 5:

5-Fluoro-3-(1-hydroxypentyl)phenol

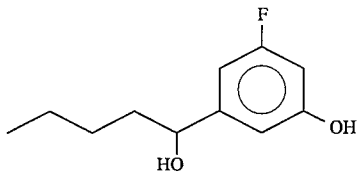

Following the procedure described for Phenol 2, Step 2 and for Phenol 1, Step 3, but substituting valeraldehyde for 3-pentanone, the title compound was obtained.

$^1$H NMR (300 MHz, Acetone-d$_6$); δ0.9 (t, 3H); 1.2–1.4 (m, 4H); 1.6–1.7 (m, 2H); 4.6 (t, 1H); 6.45 (d, 1H); 6.6 (d, 1H); 6.7 (s, 1H); 7.95 (s, 1H).

PHENOL 6:

5-Fluoro-3-{1-hydroxy-1-[N-(2-trimethylsilylethoxymethyl)imidazol-2-yl]propyl}phenol

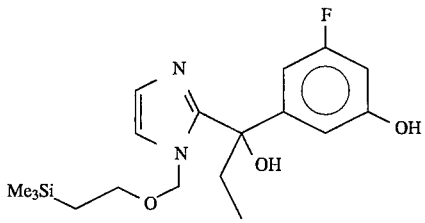

Step 1:

3-Benzyloxy-5-fluoropropiophenone

Following the procedure described for Phenol 2, Step 1, but substituting 3,5-difluoropropiophenone for 1-bromo-3,5-difluorobenzene and benzyl alcohol for 3,4-dimethoxybenzyl alcohol as starting material, the title compound was obtained.

Step 2:

5-Fluoro-3-{1-hydroxy-1-[N-(2-trimethylsilylethoxymethyl)imidazol-2-yl]propyl}(O-benzyl)phenol To a stirred solution of SEM-imidazole, (*Tet. Lett.* 26, 6273, 1985) (252 mg, 1.27 mmol) in THF (5 mL) at −78° C. under N$_2$ BuLi (857 µl, 1.4M, 1.27 mmol) was added dropwise. The reaction mixture was stirred at −78° C. for 20 min. and the ketone from Step 1 (274 mg, 1.06 mmol) was added dropwise. The reaction mixture was stirred at −78° C. for 30 min. and then quenched with a 25% solution of NH$_4$OAc, concentrated and extracted with EtOAc. The organic phase was washed with brine, dried over MgSO$_4$, filtered and evaporated to give an oil as the crude compound. The oil was purified by a flash silica column using hexane and EtOAc 9:1 as the eluant. The title compound was obtained as a transparent oil (188 mg, 39%) and used as such for the next step.

Step 3:

5-Fluoro-3-{1-hydroxy-1-[N-(2-trimethylsilylethoxymethyl)imidazol-2-yl]propyl}phenol Following the procedure described for Phenol 1, Step 3 but substituting 5-fluoro 3-{1-hydroxy-1-[N-(2-trimethylsilylethoxymethyl)imidazol- 2-yl]propyl}(O-benzyl)phenol from Step 2 for 5-fluoro-3-[1-hydroxy-1-(thiazol-2-yl)propyl](O-benzyl)phenol, the title compound was obtained as an oil.

¹H NMR (400 MHz, CDCl₃); δ0.03 (s, 9H); 0.7–0.8 (1t, 3H); 0.8–0.9 (1t, 2H); 1.9–2.25 (m, 1H); 2.30–2.40 (m, 1H); 3.12–3.22 (m, 1H); 3.30–3.40 (m, 1H); 4.08 (s, 1H); 4.95 (s, 2H); 6.04 (s, 1H); 6.45–6.52 (d, 1H); 6.65 (s, 1H); 6.99 (s, 1H); 6.72–7.0 (d, 1H).

PHENOL 7:

3-[1-Hydroxy-1-(thiazol-2-yl)propyl]phenol

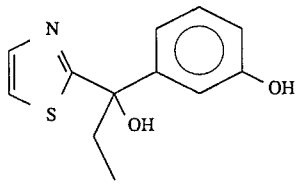

Step 1:

3-Bromo-(O-tert-butyldimethylsilyl)phenol

To a solution of 3-bromophenol (50 g, 289 mmol) in 340 mL DMF was added Et₃N (35 g, 347 mmol) and tert-butyldimethylsilyl chloride (52 g, 347 mmol). The mixture was stirred for 0.5 h, and then diluted with ET₂O (2 L). The organic phase was washed with 5% aqueous HCl and brine, and dried over MgSO₄. Flash chromatography using hexane:EtOAc (95:5) gave 80.1 g (96%) of product.

Step 2:

3-[1-Hydroxy-1-(thiazol-2-yl)propyl]-(O-tert-butyldimethylsilyl)phenol

Following the procedure described for Phenol 2, Step 2, but substituting 3-bromo-(O-tert-butyldimethylsilyl)phenol from Step 1 for 1-bromo-3-(3,4-dimethoxybenzyloxy)-5-fluoro benzene and 1-(thiazol-2-yl)propanone from Phenol 1, Step 1, for 3-pentanone, the title compound was obtained.

Step 3:

3-[1-Hydroxy-1-(thiazol-2-yl)propyl]phenol

To a solution of compound from Step 2 (5.57 g, 15.96 mmol) in THF (40 mL) them was added n-Bu₄NF 1M in THF (18 mL); the mixture was stirred at r.t. for 30 min., then H₂O (10 mL) was added. The mixture was concentrated to a small volume, the residue extracted with EtOAc, the extract washed twice with brine, dried and evaporated to a residue which was chromatographed on silica gel, eluting with a 1:1 mixture of EtOAc and hexane, to afford the title product as a white solid (2.59 g) m.p. 145°–146° C.

PHENOL 8:

3-(1-Hydroxy-1-phenylpropyl)phenol

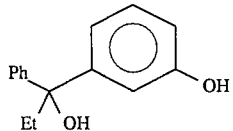

Step 1:

3-Bromo(O-tert-butyldiphenylsilyl)phenol

Following the procedure described for Phenol 7, Step 1 but substituting tert-butyldiphenylsilyl chloride for tert-butyldimethylsilyl chloride the title compound was obtained.

Step 2:

3-(1-Hydroxypropyl)(O-tert-butyldiphenylsilyl)phenol

Following the procedure described for Phenol 2, Step 2 but substituting 3-bromo(O-tert-butyldiphenylsilyl)phenol from Step 1-for 1-bromo-3-(3,4-dimethoxybenzyloxy)-5-fluorobenzene and propionaldehyde for 3-pentanone, the title compound was obtained.

Step 3:

3-(tert-Butyldiphenylsilyloxy)propiophenone

To a solution of 3-(1-hydroxypropyl)(O-tert-butyldiphenylsilyl)phenol (11.7 g, 30 mmol) in CH₂Cl₂ (300 mL) at 0° C. was added molecular sieves powder (8 g, flame dried) followed by PCC (18 g, 84 mmol). The reaction mixture was stirred at r.t. for 1 h then poured on a silica gel column and eluted with ET₂O to give the title compound as an oil (10.8 g, 93%).

Step 4:

3-(1-Hydroxy-1-phenylpropyl) (O-tert-butyldiphenylsilyl)phenol

To a solution of 3-(tert-butyldiphenylsilyloxy)propiophenone (410 mg, 1.06 mmol) in THF (6 mL) at −20° C. was added PhMgBr (2M in Et₂O, 2.0 mL, 4 mmol) dropwise. The reaction mixture was stirred at r.t. for the night, then quenched with saturated NH₄Cl at 0° C. The organic phase was extracted with EtOAc washed with H₂O, brine, dried (MgSO₄) and the solvent evaporated to afford the title compound as an oil which was used as such in the next step.

Step 5:

3-(1-Hydroxy-1-phenylpropyl)phenol

Following the procedure described for Phenol 7, Step 3, but substituting 3-(1-hydroxy-1-phenylpropyl)(O-tert-butyldiphenylsilyl)phenol from Step 4 for 3-[1-hydroxy-1-(thiazol-2-yl)propyl](O-tertbutyldimethylsilyl)phenol, the title compound was obtained.

¹H NMR (300 MHz, CDCl₃); δ0.85 (t, 3H); 2.3 (q, 2H); 6.65 (m, 1H); 6.9 (m, 2H); 7.1–7.4 (m, 6H).

PHENOL 9:

3-(3-Hydroxy-2-methylpentyl))phenol

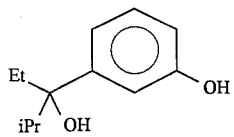

Following the procedure for Phenol 8, Step 4 and for Phenol 7, Step 3 but substituting isopropylmagnesium chloride in THF (Aldrich) for phenylmagnesium bromide, the title compound was obtained.

¹H NMR (300 MHz, Acetone-d₆); δ0.64–0.69 (m, 6H); 0.93 (d, 3H); 1.83 (m, 2H); 1.97 (m, 1H); 3.27 (s, 1H); 6.64 (dd, 1H); 6.84 (d, 1H); 6.95 (m, 1H); 7.10 (t, 1H); 7.99 (s, 1H).

PHENOL 10:

3-(2,2-Dimethyl-3-hydroxypentyl)phenol

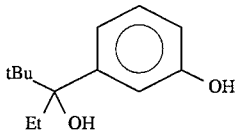

Following the procedure described for Phenol 8, Step 4 and Phenol 7, Step 3 but substituting tert-butylmagnesium chloride in THF (Aldrich) for phenylmagnesium bromide, the title compound was obtained.

$^1$H NMR (300 MHz, Acetone-$d_6$); δ0.67 (t, 3H); 0.90 (s, 9H); 1.83 (m, 1H); 2.17 (m, 1H); 3.29 (s, 1H); 6.66 (dd, 1H); 6.87 (d, 1H); 6.97 (s, 1H); 7.09 (t, 1H); 8.00 (s, 1H).
PHENOL 11:

3-[1-Hydroxy-1-(pyridin-2-yl)propyl]phenol

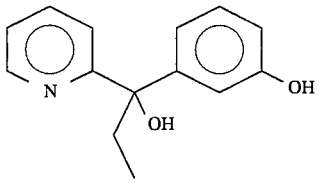

Step 1:

3-[1-Hydroxy-1-(pyridin-2-yl)propyl] (O-tert-butyldiphenylsilyl)phenol n-BuLi (2.4M in hexane, 674 μL, 1.62 mmol) was added dropwise (15 min.) to 2-bromopyridine (147 μL, 1.54 mmol) in THF (5 mL) at –78° C. and under Ar. The solution was stirred for 40 min. at this temperature. The 3-(tert-butyldiphenylsilyloxy)propiophenone (499 mg, 1.28 mmol) from Phenol 8, Step 3 in THF (2 mL) was then added dropwise (10 min.). The mixture was kept at –78° C. for 30 min. and allowed to warm to 0° C. After 20 min. the reaction was quenched with a saturated NH$_4$Cl solution and extracted with EtOAc (3×). The combined organics were washed with 25% NH$_4$OAc buffer, H$_2$O, brine, dried (MgSO$_4$) and concentrated to give an off-white gum, that was purified by column chromatography on silica gel (EtOAc/hexane 1:9), affording the title compound as a colorless gum (563 mg, 94%).
Step 2:

3-[1-Hydroxy-1-(pyridin-2-yl)propyl]phenol

Following the procedure described for Phenol 7, Step 3 but substituting 3-[1-hydroxy-1-(pyridin-2-yl)propyl](O-tert-butyldiphenylsilyl)phenol from Step 1 for 3-[1-hydroxy-1-(thiazol-2-yl)propyl](O-tertbutyldimethylsilyl)phenol, the title compound was obtained.

$^1$H NMR (300 MHz, Acetone-$d_6$); δ0.80 (t, 3H); 2.30 (q, 2H); 5.47 (s, 1H); 6.63 (m, 1H); 7.04–7.10 (m, 3H); 7.22 (m, 1H); 7.60 (d, 1H); 7.75 (m, 1H); 8.08 (s, 1H); 8.50 (d, 1H).
PHENOL 12:

3-[1-Hydroxy-1-(furan-3-yl)propyl]phenol

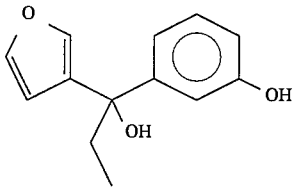

Following the procedure described for Phenol 11, Step 1, and Phenol 7, Step 3, but substituting 3-bromofuran for 2-bromopyridine the title compound was obtained.

$^1$H NMR (300 MHz, Acetone-$d_6$); δ0.82 (t, 3H); 2.13 (q, 2H); 4.15 (s, 1H); 6.35 (d, 1H); 6.66 (dd, 1H); 6.93 (m, 1H); 7.00 (m, 1H); 7.10 (t, 1H); 7.40–7.43 (m, 2H); 8.06 (s, 1H).
PHENOL 13:

3-(2-Hydroxyprop-2-yl)phenol

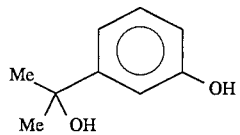

Step 1:

Methyl 3-(tert-butyldiphenylsilyloxy)benzoate

Following the procedure described for Phenol 7, Step 1, but substituting methyl-3-hydroxybenzoate for bromophenol the title compound was obtained.
Step 2:

3-(2-Hydroxyprop-2-yl)(O-tert-butyldiphenylsilyl)phenol

To a solution of methyl 3-(tert-butyldiphenylsiloxy)benzoate (Step 1)(1.1 g) in toluene (20 mL) at 0° C. was added MeMgBr in THF (Aldrich) (5.8 mL). After 1 h, additional MeMgBr (1.9 mL) was added and the mixture was stirred at r.t. for 1 h. Saturated NH$_4$Cl was added and the mixture was extracted with EtOAc. The organics were dried (MgSO$_4$), concentrated and chromatographed (silica gel; hexane/ EtOAc (4:1) to provide the title compound as an oil.
Step 3:

3-(2-Hydroxyprop-2-yl)phenol

Following the procedure described for Phenol 7, Step 3 but substituting 3-(2-hydroxyprop-2-yl)(O-tert-butyldiphenylsilyl)phenol from Step 2 for 3-[1-hydroxy-1-(thiazol-2-yl)propyl)(O-tert-butyldimethylsilyl)phenol, the title compound was obtained.

$^1$H NMR (300 MHz, Acetone-$d_6$); δ1.48 (s, 6H); 3.88 (s, 1H); 6.65 (dd, 1H); 6.95 (dd, 1H); 7.03 (dd, 1H); 7.10 (t, 1H); 8.04 (s, 1H).
PHENOL 14:

3-(3-Hydroxypent-3-yl)phenol

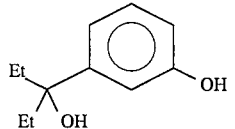

Following the procedure described for Phenol 13, Step 2 and for Phenol 7, Step 3 but substituting EtMgBr in THF (Aldrich) for MeMgBr, the title compound was obtained.

$^1$H NMR (300 MHz, Acetone-d$_6$); δ0.71 (t, 6H); 1.78 (m, 4H); 3.40 (s, 1H); 6.64 (dd, 1H); 6.85 (dd, 1H); 6.95 (dd, 1H); 7.10 (t, 1H); 8.00 (s, 1H).

PREPARATION OF THIOPHENOLS

THIOPHENOL 1:

5-Fluoro-3-(hexafluoro-2-hydroxyprop-2-yl)thiophenol

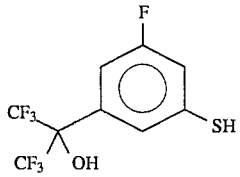

Step 1:

1,3-Difluoro-5-(hexafluoro-2-hydroxyprop-2-yl)benzene

To a solution of 1-bromo-3,5-difluorobenzene (4 g, 20.7 mmol) in dry THF (50 mL) containing magnesium (1 g, 41.5 mmol) was reflux until the Grignard reagent started to form. Then the reaction mixture was stirred at r.t. for 30 min.. Hexafluoroacetone was then bubbled in at 0° C. until approximately 3.4 g was added. The mixture was stirred for 10 min. and quenched with 25% NH$_4$OAc. The resulting mixture was extracted with EtOAc and the combined organic phase was washed with H$_2$O, brine, dried over MgSO$_4$ and evaporated to give a residue which was chromatographed on silica gel, eluting with 9:1 mixture of hexane:EtOAc to afford the title compound (4.1 g, 71%) as a white solid.

Step 2:

5-Fluoro-3-(hexafluoro-2-hydroxyprop-2-yl)-1-(2-trimethylsilylethylthio)benzene

2-Trimethylsilylethane thiol (2.9 g, 21.9 mmol) was added dropwise to a suspension of NaH (1.8 g, 43.8 mmol) in dry DMF (60 mL) and stirred for 20 min. Then 1,3-difluoro-5-(hexafluoro-2-hydroxyprop2-yl)benzene (Step 1) was added in dry DMF and the resulting reaction mixture was heated at 70° C. for 16 h. The reaction mixture was then added carefully to H$_2$O and extracted with EtOAc. The combined organic phases were washed with brine, dried and evaporated to give a residue which was chromatographed on silica gel, eluting with 95:5 mixture of hexane:EtOAc to afford the title compound (3.2 g, 55%).

Step 3:

5-Fluoro-3-(hexafluoro-2-hydroxyprop-2-yl)thiophenol

To a solution of 5-fluoro-3-(hexafluoro-2-hydroxyprop-2-yl)-1-(2-trimethylsilylethylthio)benzene (1 g, 2.54 mmol Step 2) in dry DMF (20 mL) was added tetrabutylammonium fluoride (1M in THF) (Aldrich) (6.4 mL, 6.4 mmol) and the reaction mixture was heated at 60° C. for 30 min.. The reaction mixture was then added to H$_2$O and extracted with EtOAc. The combined organic phase were washed with brine, dried and evaporated to give a residue which was chromatographed on silica gel eluting with 8:2 mixture of hexane:EtOAc to afford the title compound (330 mg, 44%).

$^1$H NMR (400 MHz, CDCl$_3$); δ3.7 (s, 1H), 7.1 (d, 1H); 7.2 (d, 1H); 7.4 (s, 1H).

THIOPHENOL 2:

5-Fluoro-3-[3-hydroxy-3-(thiazol-2-yl)propen-3-yl]thiophenol

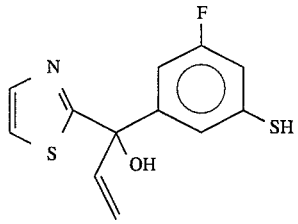

Step 1:

3,5-Difluoro-α-(thiazol-2-yl)benzenemethanol

Following the procedure described for Thiophenol 1, Step 1, but substituting the 2-thiazole carboxaldehyde (*Synthesis*, 998, 1987) for hexafluoroacetone as starting material, the title compound was obtained as a liquid.

Step 2:

(3,5-Difluorophenyl)(thiazol-2-yl)methanone

To a suspension of CrO$_3$ (1.1 g, 11 mmol) in CH$_2$Cl$_2$ at r.t. was added pyridine (1.8 mL, 22 mmol) and the resulting mixture was stirred for 20 min.. The alcohol from Step 1 in CH$_2$Cl$_2$ was added and the resulting mixture was stirred for 16 h. Then ET$_2$O was added and the resulting mixture was filtered through silica gel and washed with Et$_2$O. After evaporation the residue was chromatographed on silica gel eluting with 7:3 mixture of hexane:EtOAc to give 1.66 g (90%) of the title compound.

Step 3:

1,3-Difluoro-5-[3-hydroxy-3-(thiazol-2-yl)propen-3-yl]benzene

To a solution of (3,5-difluorophenyl)(thiazol-2-yl)methanone (1 g, 4.4 mmol, Step 2) in dry THF (40 mL) was added at 0° C. (4.4 mL, 4.4 mmol) of a 1.0M THF solution of vinyl magnesium bromide (Aldrich). The reaction mixture was stirred for 30 min. and then transferred to a 1N aqueous HCl solution. The resulting mixture was extracted with EtOAc and the combined organic phase were washed with brine, dried over MgSO$_4$ and evaporated to give a residue which was chromatographed on silica gel eluting with 85:15 mixture of hexane: EtOAc to afford 635 mg (56%) of the title compound.

Step 4:

5-Fluoro-3-[$^3$-hydroxy-3-(thiazol-2-yl)propen-3-yl]-1-(2-trimethylsilylethylthio)benzene Following the procedure described for Thiophenol 1, Step 2, but substituting the 1,3-difluoro-5-[3-hydroxy-3-(thiazol-2-yl)propen-3 -yl]benzene from Step 3 for 1,3-difluoro-5-(hexafluoro-2-hydroxyprop-2 -yl)benzene as starting material, the title compound was obtained as an oil.

Step 5:

5-Fluoro-3-[3-hydroxy-3-(thiazol-2-yl)propen-3-yl]thiophenol

Following the procedure described for Thiophenol 1, Step 3, but substituting the 5-fluoro-3-[3-hydroxy-3-(thiazol-2-yl)propen-3-yl]-1-(2-trimethylsilylethylthio)benzene from Step 4 for 5-fluoro-3-(hexafluoro- 2-hydroxyprop-2-yl)-1-(2-trimethylsilylethylthio)benzene as starting material, the title compound was obtained.
THIOPHENOL 3:

5-Fluoro-3-(3-hydroxypent-3-yl)thiophenol

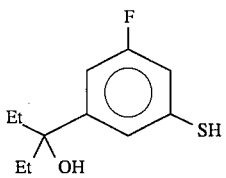

Step 1:

3-Bromo-5-fluoro-1-(2-trimethylsilylethylthio)benzene

Following the procedure described for Thiophenol 1, Step 2, but substituting 1-bromo-3,5-difluorobenzene (Aldrich) for 1,3-difluoro-5-(hexafluoro-2-hydroxyprop-2-yl)benzene as starting material, the title compound was obtained.
Step 2:

5-Fluoro-3-(3-hydroxypent-3-yl)-1-(2-trimethylsilylethylthio)benzene

Following the procedure described for Thiophenol 1, Step 1, but substituting the 3-bromo-5-fluoro-1-(2-trimethylsilylethylthio)benzene from Step 1, for 1-bromo-3,5-difluorobenzene and 3-pentanone for hexafluoroacetone as starting material the title compound was obtained.
Step 3:

5-Fluoro-3-(3-hydroxypent-3-yl)thiophenol

Following the procedure described for Thiophenol 1, Step 3 but substituting the 5-fluoro-3-(3-hydroxypent-3-yl)-1-(2-trimethylsilylethylthio)benzene from Step 2 for 5-fluoro-3-(hexafluoro-2-hydroxyprop-2-yl)-1-(2-trimethylsilyethylthio)benzene as starting material, the title compound was obtained.
$^1$H NMR (300 MHz, Acetone-d$_6$); δ0.71 (t, 6H); 1.79 (m, 4H); 3.71 (s, 1H); 4.49 (s, 1H); 6.92–6.98 (m, 2H); 7.19 (m, 1H).
THIOPHENOL 4:

5-Fluoro-3-(1-hydroxy-1-phenyl-2,2,2-trifluoroethyl)thiophenol

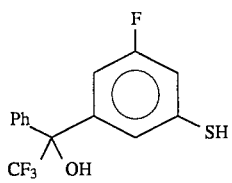

Step 1:

1,3-Difluoro-5-(1-phenyl-1-trimethylsilyloxy-2,2,2-trifluoroethyl)benzene

To a solution of 3,5-difluorobenzophenone (2.27 g, 10.4 mmol) in THF (5 mL) at 0° C. was added trimethyl(trifluoromethyl)silane (0.5M in THF, 26 mL, 13.0 mmol) and a pinch of solid n-Bu$_4$NF. The mixture was stirred at r.t. for 17 h. Sat. aqueous NH$_4$Cl was added, the layers were separated and the organic phase was extracted with EtOAc (3×20 mL). The combined organic layers were washed with brine and dried over anhydrous MgSO$_4$. Removal of the solvent and chromatography using hexane:EtOAc (95:5) gave 3.06 g of the title compound.
Step 2:

5-Fluoro-3-(1-hydroxy-1-phenyl-2,2,2-trifluoroethyl)thiophenol

Following the procedure described for Thiophenol 1, Steps 2 and 3 but substituting the product from Step 1 for 1,3-difluoro-5-(hexafluoro- 2-hydroxyprop-2-yl)benzene as starting material, the title compound was obtained.
THIOPHENOL 5:

5-Fluoro-3-(thiazol-2-ylcarbonyl)thiophenol

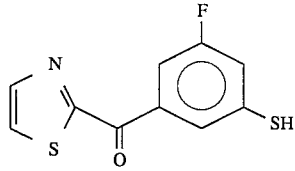

Step 1:

(3-Methylthio-5-fluorophenyl)(thiazol-2-yl)methanone

To a solution of (3,5-difluorophenyl)(thiazol-2-yl)methanone from Thiophenol 2, Step 2, (1.09 g, 4.84 mmol) in DMF (4.8 mL) was added sodium thiomethoxide (0.34 g, 4,84 mmol). The mixture was stirred for 4 h at r.t., then added to sat. aqueous NH$_4$Cl (100 mL) and extracted with EtOAc. The combined organic layers were washed with brine and dried over anhydrous MgSO$_4$. Evaporation of the solvent and chromatography using hexane:EtOAc (90:10) gave 0.80 g of the title product.
Step 2:

(3-Methylsulfinyl-5-fluorophenyl)(thiazol-2-yl)methanone

To a solution of sulfide from Step 1 (0.76 g, 2.99 mmol) in MeOH (1.5 mL) and CH$_2$Cl$_2$ (6 mL) at 0° C. was added the magnesium salt of monoperoxyphthalic acid (1.11 g, 1.80 mmol). The mixture was stirred at 0° C. for 1.25 h and then sat. aqueous NaHCO$_3$ was added. The layers were separated and the aqueous phase was extracted with CH$_2$Cl$_2$. The combined organic layers were washed with H$_2$O and dried over anhydrous MgSO$_4$. Evaporation of the solvent and chromatography using toluene:EtOAc (25:75) gave 0.70 g of the title compound.
Step 3:

5-Fluoro-3-(thiazol-2-ylcarbonyl)thiophenol

To a solution of the sulfoxide from Step 2 (0.35 g, 1.29 mmol) in dichloroethane (2.6 mL) was added TFAA (2.6 mL). The mixture was stirred at 80° C. for 0.5 h, cooled and evaporated. The residue was dissolved in MeOH: Et$_3$N (1:1, 5 mL). The solvent was evaporated and taken up again in MeOH/Et₃N. After evaporation of the solvent and chromatography using hexane:EtOAc (70:30) 0.28 g of the title compound was obtained.

¹H NMR (300 MHz, Acetone-d₆); δ7.5 (dd, 1H); 8.0 (d, 1H); 8.0–8.3 (2d, 3H).

THIOPHENOL 6:

5-Fluoro-3-[1-hydroxy-1-(thiazol-2-yl)ethyl]thiophenol

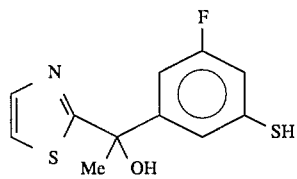

Following the procedure described for Thiophenol 2, Step 3 and Thiophenol 5, Steps 2 and 3 but substituting the ketone from Thiophenol 5, Step 1 for (3,5-difluorophenyl)(thiazol-2-yl)-methanone and methylmagnesium bromide (Aldrich) in THF for vinylmagnesium bromide as starting material, the title compound was obtained.

THIOPHENOL 7:

5-Fluoro-3-[1-hydroxy-2-methyl-1-(thiazol-2-yl)propyl]thiophenol

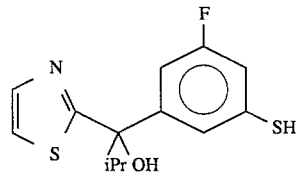

Following the procedure described for Thiophenol 2, Step 3 and Thiophenol 5, Steps 2 and 3 but substituting the ketone from Thiophenol 5, Step 1 for (3,5-difluorophenyl)(thiazol-2-yl)-methanone and isopropylmagnesium bromide (Aldrich) in THF for vinylmagnesium bromide as starting material the title compound was obtained.

THIOPHENOL 8:

5-Fluoro-3-[1-hydroxy-1-(thiazol-2-yl)propyl]thiophenol

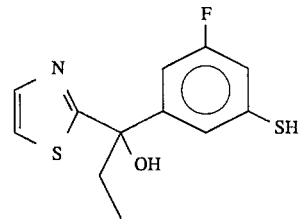

Following the procedure described for Thiophenol 2, Step 3 and thiophenol 5, Steps 2 and 3 but substituting the ketone from Thiophenol 5, Step 1 for (3,5-difluorophenyl)(thiazol-2-yl)methanone and ethylmagnesium bromide in THF (Aldrich) for vinylmagnesium bromide as starting material the title compound was obtained. Mass spec. 270 (MH⁺).

THIOPHENOL 9:

5-Fluoro-3-(1-hydroxy-1-phenylpropyl)thiophenol

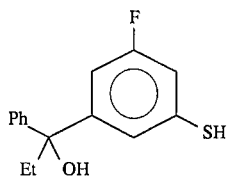

Following the procedure described for Thiophenol 2, Step 3 and Thiophenol 1, Steps 2 and 3 but substituting 3,5-difluoropropiophenone (Lancaster) for (3,5-difluorophenyl)(thiazol-2-yl)methanone and phenylmagnesium bromide in THF (Aldrich) for vinylmagnesium bromide as starting material the title compound was obtained.

THIOPHENOL 10:

5-Fluoro-3-(decafluoro-3-hydroxypent-3-yl)thiophenol

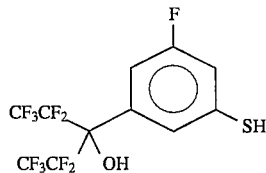

Step 1:

3,5-Difluoro-1-(decafluoro-3-hydroxypent-3yl)benzene

A three-necked flash was charged with 9.61 g (39.1 mmol) of pentafluoroethyl iodide at −78° C. under a dry nitrogen atmosphere. 50 mL of ET₂O was added followed by 1.38 g (7.82 mmol) of 3,5-difluorobenzoyl chloride (Aldrich). To the stirred solution was added 27.9 mL (39.1 mmol) of a 1.4M solution of methyllithium/lithium bromide complex in diethyl ether. The reaction mixture was stirred for 0.5 h and then poured into a separating funnel containing 100 mL of a 5% aqueous hydrochloric acid solution and 50 mL of diethyl ether. After the layers were shaken and separated, the aqueous layer was further extracted with 25 mL of diethyl ether, and the combined extracts were dried over anhydrous magnesium sulfate. After filtration and solvent removal on a rotary evaporator, the product was distilled under reduced pressure to give 2.44 g (82%) of the tertiary alcohol, bp 70°–75° C. (5 mm).

Step 2:

5-Fluoro-3-(decafluoro-3-hydroxypent-3-yl)thiophenol

Following the procedure described for Thiophenol 1, Step 2 and 3, but substituting 3,5-Difluoro-1-(decafluoro-3-hydroxypent-3 -yl)benzene from Step 1 for 1,3-difluoro-5-(hexafluoro-2-hydroxyprop-2 -yl)benzene, the title compound was obtained.

PREPARATION OF ALCOHOLS

Alcohol 1:

3-[1-Hydroxy-1-(thiazol-2-yl)propyl]benzyl alcohol

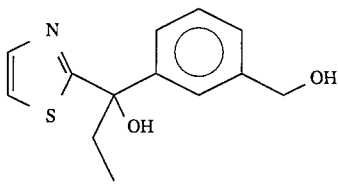

Step 1:

3-Bromo(O-tert-butyldiphenylsilyl)benzyl alcohol

Following the procedure described for Phenol 7, Step 1 but substituting 3-bromo-benzyl alcohol for 3-bromophenol and tert-butyldiphenylsilyl chloride for tert-butyldimethylsilyl chloride the title compound was obtained.

Step 2:

3-[1-Hydroxy-1-(thiazol-2-yl)propyl]benzyl alcohol

Following the procedure described for Phenol 2, Step 2 and for Phenol 7, Step 3 but substituting the compound from Step 1 for 1-bromo-3-(3,4-dimethoxybenzyloxy)-5-fluorobenzene and 1-(thiazol-2 -yl)propanone (from Phenol 1, Step 2) for 3-pentanone the title compound was obtained.

$^1$H NMR (400 MHz, CDCl$_3$); δ0.9 (t, 3H); 2.4 (m, 2H); 3.82 (s, 1H), 4.7 (s, 2H); 7.3 (m, 3H); 7.52 (dd, 1H); 7.63 (s, 1H); 7.7 (d, 1H).

Alcohol 2:

6-(3-Hydroxypent-3-yl)pyridin-2-methanol

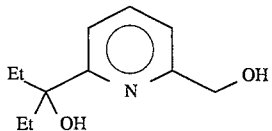

Step 1:

6-Bromopicolinic acid

To a suspension of 2,6-dibromopyridine (59 g, 0.25 mol) in ET$_2$O (600 mL) at −70° C. there was added slowly n-BuLi 2.12M in hexanes (118 mL, 0.25 mol); the resulting mixture was stirred in the cold until a solution was obtained (45 min.); this mixture was poured onto a slurry of crushed dry ice (200 g) in ET$_2$O (500 mL). The resulting suspension was allowed to warm up, then it was extracted with H$_2$O (500 mL, then 250 mL). The combined aqueous extracts were extracted with Et$_2$O, then acidified with 12N HCl, affording a precipitate which was filtered. This beige solid was washed with H$_2$O and dried to afford the title acid (32 g), m.p. 186°–189° C.

Step 2:

Ethyl 6-Bromo-2-picolinate

To a solution of 6-bromopicolinic acid from Step 1 (92 g, 0.455 mol) and Et$_3$N (69 g, 0.68 mol) in THF (1.1 L) at 0° C. there was slowly added ethyl chloroformate (61.6 g, 0.57 mol). The resulting suspension was stirred at 0° C. for 15 min., EtOH (250 mL) was added, and the mixture was stirred at r.t. overnight. After filtration, the filtrate was evaporated down, the residue was taken up in ET$_2$O (1 L) and filtered again. The filtrate on evaporation of the solvents afforded the title compound as an oil which was immediately used as such.

Step 3:

6-Bromopyridin-2-methanol

The ester from Step 2 was dissolved in THF (1.2 L), the solution cooled to 0° C., and under a N$_2$ atmosphere, there was slowly added LiAlH$_4$ (20 g) over 1 h. After a further 30 min., the mixture was quenched carefully with sat'd aqueous NH$_4$Cl (250 mL). The granular salts were filtered off, washed with EtOAc, and the filtrate was dried over MgSO$_4$, and evaporated to afford the title alcohol (85 g) as an oil.

Step 4:

6-Bromo(O-tert-butyldiphenylsilyl)pyridin-2-methanol

Following the procedure described for Phenol 7, Step 1 but substituting tert-butyldiphenylsilyl chloride for tert-butyldimethylsilyl chloride and 6-bromopyridin-2-methanol from Step 1 for 3-bromophenol, the title compound was obtained as a yellow oil.

Step 5:

6-(3-Hydroxypent-3-yl)pyridin-2-methanol

Following the procedure described for Phenol 2, Step 2 and for Phenol 7, Step 3, but substituting 6-bromo(O-tert-butyldiphenylsilyl)pyridin- 2-methanol form Step 4 for 1-bromo-3-(3,4-dimethoxybenzyloxy)- 5-fluorobenzene, the title compound was obtained.

$^1$H NMR (300 MHz, Acetone-d$_6$); δ0.63 (t, 6H); 1.81 (m, 4H); 4.58 (s, 1H); 4.71 (s, 2H), 4.91 (s, 1H), 7.46 (dd, 2H); 7.78 (t, 1H).

Alcohol 3:

6-(Hexafluoro-2-hydroxyprop-2-yl)pyridin-2-methanol

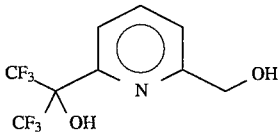

Following the procedure described for Phenol 2, Step 2 and for Phenol 7, Step 3 but substituting 6-bromo-(O-tert-butyldiphenylsilyl)pyridin- 2-methanol (from Alcohol 2, Step 4) for 1-bromo-3-(3,4-dimethoxybenzyloxy)-5-fluorobenzene and hexafluoroacetone for 3 -pentanone, the title compound was obtained. m.p.: 62°–63° C.

Alcohol 4:

6-[1-Hydroxy-1-(thiazol-2-yl)propyl]pyridin-2-methanol

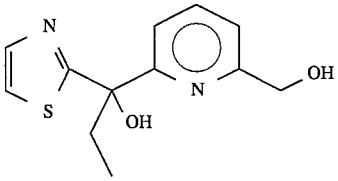

Following the procedure described for Phenol 2, Step 2 and for Phenol 7, Step 3 but substituting 6-bromo(O-tert-butyldiphenylsilyl)pyridin- 2-ylmethanol (from Alcohol 2, Step 4) for 1-bromo-3-(3,4-dimethoxy)benzyloxy-5-fluorobenzene and 1-(thiazol-2-yl)propanone (from Phenol 1, Step 2) for 3-pentanone the title compound was obtained.
Alcohol 5:

6-[1-Methoxy-1-(thiazol-2-yl)propyl]pyridin-2-methanol

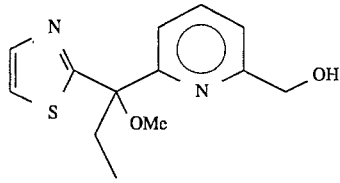

Step 1:

6-[1-Hydroxy-1-(thiazol-2-yl)propyl]
(O-tert-butyldimethylsilyl)pyridin- 2-methanol Following the procedure described for Phenol 2, Step 2 but substituting 6-bromo-(O-tert-butyldimethylsilyl)pyridin-2-ylmethanol for 1-bromo-3-(3,4-dimethoxybenzyloxy)-5-fluorobenzene and 1-(thiazol-2 -yl)propanone (from Phenol 1, Step 2) for 3-pentanone, the title compound was obtained.
Step 2:

6-(1-Methoxy-1-(thiazol-2-yl)propyl)
(O-tert-butyldimethylsilyl)pyridin- 2-methanol To a solution of alcohol from Step 1 (740 mg, 2.03 mmol) in 20 mL THF at 0° C. was added KH (466 mg, 4.06 mmol, 35% in oil). After 10 min. MeI (1.44 g, 10.1 mmol) was added dropwise. The solution was stirred for 30 min. at 0° C., then poured into an aqueous saturated $NH_4C_1$. The aqueous layer was extracted with EtOAc (3×25 mL) and the combined organic layers were washed with brine and dried over anhydrous $MgSO_4$. Evaporation of the solvent and flash chromatography on silica gel (hexane:EtOAc=9:1) gave the title compound (1.2 g) which was used directly in the next step.
Step 3:

6-(1-Methoxy-1-(thiazol-2-yl)propyl)
pyridin-2-ylmethanol

Following the procedure described for Phenol 7, Step 3 but substituting the silyl ether from Step 2 for 3-(1-hydroxy-1-(thiazol-2-yl)propyl)(O-tert-butyldimethylsilyl)phenol the title compound was obtained.

PREPARATION OF BROMOPYRIDINES

Bromopyridine 1:

2-Bromo-6-(hexafluoro-2-hydroxyprop-2-yl)pyridine

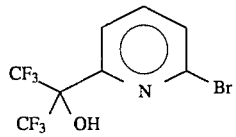

Following the procedure described for Alcohol 2, Step 1 but substituting hexafluoroacetone for $CO_2$, the title compound was obtained. m.p.: 67°–69° C.
Bromopyridine 2:

2-Bromo-6-(3-hydroxypent-3-yl)pyridine

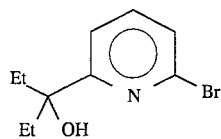

Following the procedure described for Alcohol 2, Step 1 but substituting 3-pentanone for $CO_2$, the title compound was obtained.
$^1$H NMR (300 MHz, $CDCl_3$); δ0.70 (t, 6H); 1.81 (m, 4H); 4.29 (s, 1H); 7.21 (d, 1H); 7.35 (d, 1H); 7.56 (t, 1H).
Bromopyridine 3:

2-Bromo-6-[1-hydroxy-1-(thiazol-2-yl)propyl]pyridine

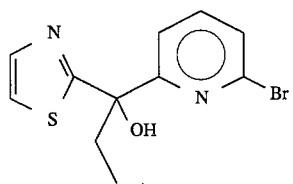

Following the procedure described for Alcohol 2, Step 1, but substituting 1-(thiazol-2-yl)-1-propanone (from Phenol 1, Step 2) for $CO_2$, the title compound was obtained.
$^1$H NMR (400 MHz, $CDCl_3$); δ0.83 (t, 1H); 2.25 and 2.37 (2m, 2H); 5.97 (s, 1H, OH); 7.22 (d, 1H); 7.39 (d, 1H); 7.58 (t, 1H); 7.74 (d, 1H); 7.81 (d, 1H).

PREPARATION OF COUMARINS

Coumarin 1:

7-Bromomethyl-4-(furan-3-yl)coumarin

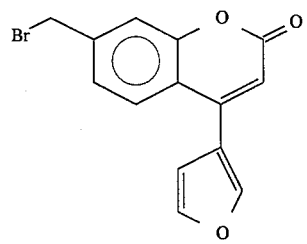

Step 1:

3-Acetoxytoluene

To a solution of m-cresol (Aldrich) (80 g, 0.74 mol) in dry $CH_2Cl_2$ (300 mL) was added pyridine (71 mL, 0.89 mol) and at 0° C. was added dropwise acetyl chloride (58 mL, 0.81 mol). The reaction mixture was stirred for 1 h and then diluted with more $CH_2Cl_2$. The organic phase was washed successively with HCl 1N (3×), brine, dried over $MgSO_4$ and evaporated. The residue was distilled under vacuum to give 108 g (97%) of the title compound.
Step 2:

2-Hydroxy-4-methylacetophenone

To 50 g (0.33 mol) of 3-acetoxytoluene from Step 1 was added $AlCl_3$ (60 g, 0.45 mol) and the resulting mixture was heated at 165° C. for 20 min., then cooled at 0° C. and HCl 1N was carefully added followed by Et₂O. The aqueous phase was extracted 5× with ET₂O and the combined organic phase wash washed with brine, dried over MgSO₄ and evaporated. The residue was distilled under vacuum to give 42.2 (84%) of the title compound.

Step 3:

4-Hydroxy-7-methylcoumarin

A solution of 42 g (0.28 mol) of 2-hydroxy-4-methylacetophenone in benzene (150 mL) was added over 30 min. to a suspension of NaH (50% oil), 30 g, 0.63 mol) in 400 mL of benzene at reflux. Then, diethylcarbonate (67.8 mL, 0.56 mol) in benzene (500 mL) was added over 15 min.. The reaction mixture was refluxed for 16 h and more NaH (13 g, 0.28 mol) was added followed by more diethylcarbonate (33 g, 0.28 mol). After another 6 h at reflux the reaction mixture was cooled to r.t. and HCl (2N) was added (1.5 L) to form a white precipitate. The solid was then filtered and added to a solution of NaOH (4N) (800 mL). The resulting basic solution was then extracted with ET₂O (2×500 mL) and the basic solution acidified with HCl conc. to give a white solid which after filtration and dried gave 38.7 g (79%) of the title compound.

Step 4:

7-Methyl-4-trifluoromethanesulfonyloxycoumarin

To a solution of 4-hydroxy-7-methylcoumarin (10 g, 56.8 mmol) in CH₂Cl₂ (250 mL) was added Et₃N (9.5 mL, 68.2 mmol) and at 0° C. was added trifluoromethanesulfonic anhydride (11.5 mL, 68.2 mmol). The reaction mixture was stirred for 16 h. Then more CH₂Cl₂ was added and the reaction mixture washed with HCl 1N (3×), brine dried over MgSO₄ and evaporated. The residue was purified by flash chromatography on silica gel using hexane:EtOAc 9:1 to give 10.6 g (61%) of the title compound.

Step 5:

4-(Furan-3-yl)-7-methylcoumarin

To a solution of 3-bromofuran (1.9 g, 12.7 mmol) in dry ET₂O (30 mL) at −70° C. was added BuLi in hexane (1.9M, 6.7 mL, 12.7 mmol) and the resulting mixture was stirred for 20 min.. Trimethyl borate (Aldrich) (1.4 mL, 12.7 mmol) was added dropwise and the mixture stirred for 20 min.. A solution of the triflate from Step 4 in THF: H₂O (24 mL: 6 mL) containing (Ph₃P)₄Pd (1.1 g, 0.97 mmol) was added and the reaction was heated to reflux for 16 h. The reaction mixture was cooled to r.t. and EtOAc was added and the organic phase washed with H₂O (3×), brine, dried over MgSO₄ and evaporated to give a white solid. A swish in EtOAc gave after filtration 1.8 g (82%) of the title compound.

Step 6:

7-Bromomethyl-4-(furan-3-yl)coumarin

To a solution of 4-(furan-3-yl)-7-methylcoumarin (1.2 g, 5.3 mmol) in CCl₄ (40 mL) was added NBS(1 g, 5.8 mmol) followed by AIBN (87 mg, 0.53 mmol). The resulting mixture was refluxed for 4 h, then cooled to r.t. filtered and evaporated. Purification by chromatrography on silica gel gave 682 mg (42%) of the title compound.

¹H NMR (400 MHz, CDCl₃); 4.51 (s, 2H); 6.41 (s, 1H); 6.66 (s, 1H); 7.31 (d, 1H); 7.39 (s, 1H); 7.59 (s, 1H); 7.73 (d, 1H); 7.79 (s, 1H).

Coumarin 2:

7-Bromomethyl-4-(4-fluorophenyl)coumarin

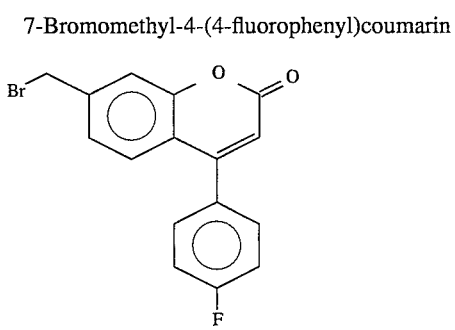

Following the same procedure described for Coumarin 1, Steps 5 and 6 but substituting 4-fluoroiodobenzene for 3-bromofuran the title compound was obtained.

Coumarin 3:

7-Bromomethyl-4-(thien-3-yl)coumarin

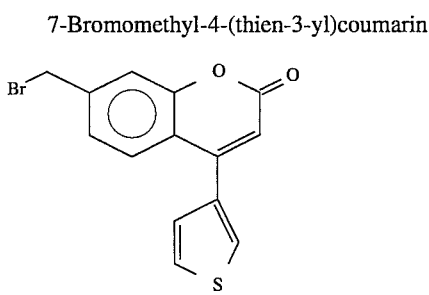

Following the same procedure described for Coumarin 1, Steps 5 and 6 but substituting 3-bromothiophene for 3-bromofuran the title compound was obtained.

Coumarins 4 to 10 were prepared following the procedure described for Coumarin 1, Steps 1 to 5 but substituting 3-bromophenol for m-cresol and substituting respectively in Step 5, 3-bromofuran, 3-bromothiophene, iodobenzene, 4-fluoroiodobenzene, 4-chloroiodobenzene, 2-trimethyl-silyl-thiazole (Fluka), 2-chloro-3-bromothiophene for 3-bromofuran, the Coumarins 4 to 10 were obtained.

Coumarin 4:

61

7-Bromo-4-(furan-3-yl)coumarin

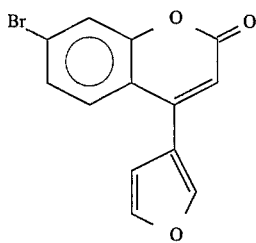

Coumarin 5:

7-Bromo-4-(thien-3-yl)coumarin

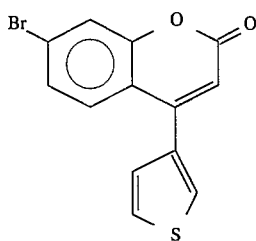

Coumarin 6:

7-Bromo-4-phenylcoumarin

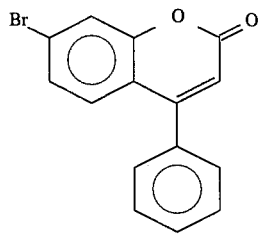

Coumarin 7:

7-Bromo-4-(4-fluorophenyl)coumarin

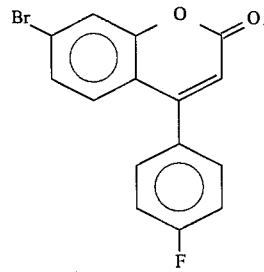

$^1$H NMR (400 MHz, CDCl$_3$); δ6.35 (s, 1H); 7.20 (d, 2H); 7.30 (d, 1H); 7.35 (d, 1H); 7.41 (m, 2H); 7.6 (s, 1H).
Coumarin 8:

62

7-Bromo-4-(4-chlorphenyl)coumarin

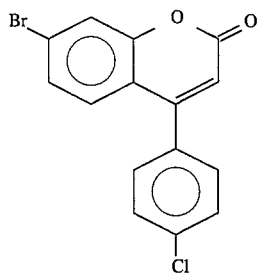

Coumarin 9:

7-Bromo-4-(thiazol-5-yl)coumarin

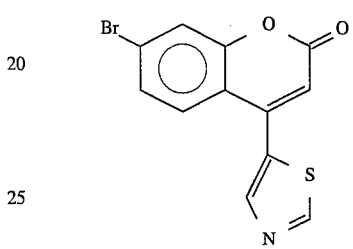

$^1$H NMR (400 MHz, CDCl$_3$); 6.52 (s, 1H); 7.52–7.55 (d, 1H); 7.58–7.62 (t, 2H); 8.14 (s, 1H); 9.0 (s, 1H).
Coumarin 10:

7-Bromo-4-(2-chlorothien-3-yl)coumarin

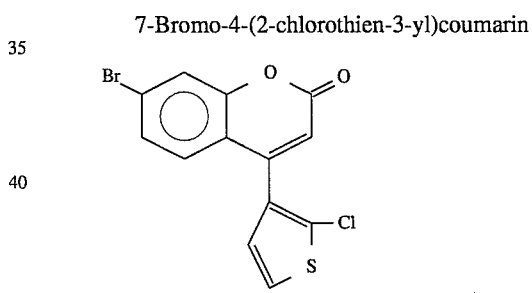

$^1$H NMR (400 MHz, Acetone-d$_6$); δ6.5 (s, 1H); 7.4 (d, 1H); 7.5–7.6 (dd, 1H); 7.65 (d, 1H); 7.7 (d, 1H); 7.8 (d, 1H).
Coumarin 11:

7-Bromo-4-(2,4-dichlorophenyl)coumarin

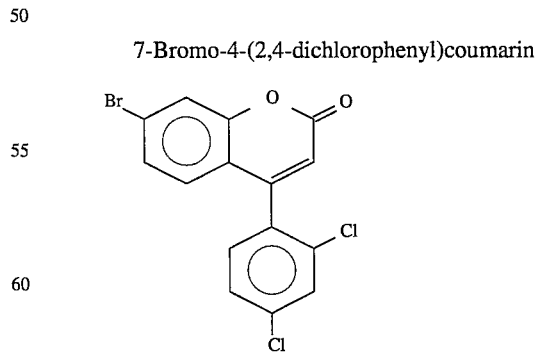

Step 1:

7-Bromo-4-(trifluoromethanesulfonyloxy)coumarin

Following the procedure described for Coumarin 1, Steps 1 to 4 but substituting 3-bromophenol for m-cresol the title compound was obtained.

Step 2:

7-Bromo-4-(2,4-dichlorophenyl)coumarin

To a solution of the triflate from Step 1 (712 mg, 1.91 mmol) in 15 ml THF was added 2,4-dichlorophenyl boronic acid (400 mg, 2.10 mmol), (Ph$_3$P)$_4$Pd (110 mg, 0.095 mmol) and aqueous Na$_2$CO$_3$ (1.91 mL, 3.82 mmol). The mixture was heated at 70° C. for 2 h, cooled and partitioned between aqueous NH$_4$Cl and EtOAc (50 mL each). The layers were separated and the aqueous phase was extracted with EtOAc (3×25 mL). The combined organic layers were dried over anhydrous MgSO$_4$. The solvent was evaporated and the residue chromatographed on silica gel (hexane: EtOAc 9:1) to give 480 mg (68%) of the title compound.

Coumarin 12:

7-Bromo-4-(3-chloro-4-fluorophenyl)coumarin

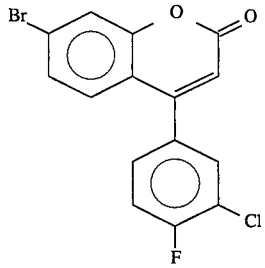

$^1$H NMR (400 MHz, Acetone-d$_6$); δ6.5 (s, 1H); 7.4–7.5 (dd, 1H); 7.5 (dd, 1H); 7.5–7.6 (d, 1H); 7.6 (dq, 1H); 7.6–7.7 (d, 1H); 7.7–7.8 (dd, 1H).

Coumarin 13:

7-Bromo-4-(3-nitrophenyl)coumarin

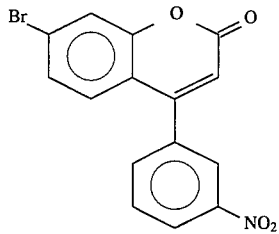

$^1$H NMR (400 MHz, Acetone-d$_6$); δ7.4 (d, 1H); 7.5 (dd, 1H); 7.7 (d, 1H); 7.9–8.0 (d, 1H); 8.0–8.1 (m, 1H); 8.4 (dt, 2H).

Coumarin 14:

7-Bromo-4-(3-trifluoromethoxyphenyl)coumarin

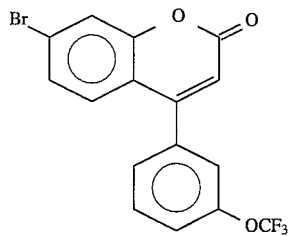

$^1$H NMR (400 MHz, Acetone-d$_6$); 7.4 (d, 1H); 7.5 (dd, 1H); 7.5–7.6 (dt, 2H); 7.6–7.7 (dt, 1H); 7.7 (d, 1H); 7.7 (d, 1H); 7.7–7.8 (ddd, 1H).

Coumarins 12 to 14 were prepared following the procedure described for Coumarin 11, Step 2 but substituting respectively 3-chloro-4-fluorophenyl boronic acid, 3-nitrophenyl boronic acid, and 3-trifluoromethoxyphenyl boronic acid for 2,4-dichlorophenyl boronic acid.

Coumarin 15:

7-Bromo-4-(pyridin-3-yl)coumarin

To a solution of 3-bromopyridine (0.10 mL) in THF (3 mL) stirred at −100° C. was added a solution of n-BuLi in hexanes (1.4M; 0.71 mL), after 10 min., the resulting yellow-green solution was treated with a solution of zinc chloride in THF (0.5M; 2 mL) and the cold bath was removed. After another 10 min., triflate from Coumarin 11, Step 1 (376 mg) and (Ph$_3$)$_4$Pd (46 mg) were added and the reaction mixture was stirred at r.t. for 1 h. Ethyl acetate was then added and the organic phase was washed successively with saturated aqueous NaHCO$_3$, H$_2$O and brine dried (MgSO$_4$), and evaporated. Flash chromatography of the residue (silica gel; hexane/EtOAc (1:3)) afforded the title compound as a yellow solid.

$^1$H NMR (400 MHz, CDCl$_3$); δ6.40 (s, 1H); 7.25 (m, 1H); 7.35 (d, 1H); 7.50 (m, 1H); 7.60 (s, 1H); 7.75 (m, 1H); 8.70 (s, 1H), 8.80 (d, 1H).

Coumarin 16:

7-Bromo-4-(pyridin-4-yl)coumarin

Following the procedure described for Coumarin 15, but substituting 4-bromopyridine for 3-bromopyridine, the title compound was obtained.

$^1$H NMR (400 MHz, CDCl$_3$); δ6.36 (s, 1H); 7.18–7.26 (d, 1H); 7.30–7.40 (m, 4H); 7.58–7.70 (m, 2H); 8.80 (d, 2H).
Coumarin 17:

7-Bromo-4-(pyridin-2-yl)coumarin

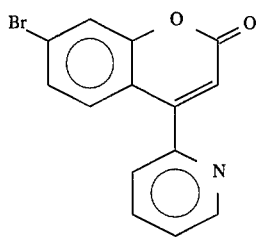

Following the procedure described for Coumarin 15, but substituting 2-bromopyridine for 3-bromopyridine, the title compound was obtained.

$^1$H NMR (CDCl$_3$, 400 MHz); δ6.50 (s, 1H), 7.35 (s, 1H); 7.45 (m, 1H), 7.55 (m, 2H), 7.65 (d, 1H); 7.90 (t, 1H); 8.80 (d, 1H).
Coumarin 18:

7-Bromo-4-trifluoromethylcoumarin

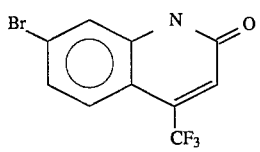

To a solution of 48% HBr (4.5 g, 26.7 mmol) (3 mL) containing 7-amino-4-trifluoromethylcoumarin (Aldrich) (2.0 g, 8.8 mmol) at −10° C. was added NaNO$_2$ (670 mg in 1 mL of H$_2$O) then Cu powder 35 mg was added. The reaction mixture was stirred at r.t. for 30 min., then heated to 100° C. for 30 min.. The reaction mixture was cooled to 0° C. and H$_2$O (25 mL) was added. The mixture was extracted with EtOAc (400 mL) and the combined organic phase was washed with brine (200 mL) dried over MgSO$_4$ and evaporated. The crude solid was purified by chromatography on silica gel using hexane:EtOAc 8:2 as eluent, to give 1.5 g (58%) of the title compound as a white solid.

$^1$H NMR (400 MHz, Acetone-d$_6$); δ7.0 (s, 1H); 7.6–7.8 (m, 3H).
Coumarin 19:

7-Bromo-4-(imidazol-1-yl)coumarin

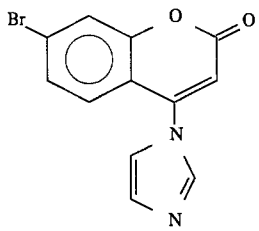

The triflate from Coumarin 11, Step 1 (373 mg, 1 mmol) was mixed with imidazole (68 mg, 1 mmol) and K$_2$CO$_3$ (330 mg, 2.5 mmol) in n-methylpyrrolidone (4.0 mL) and the reaction was heated at 120° C. for 30 min.. The reaction mixture was diluted with EtOAc, washed with brine dried over MgSO$_4$, filtered and evaporated to give an oil which was purified on a silica gel column using hexane:EtOAc 9:1 as the eluent. The title compound was obtained as a white solid, (40 mg, 15%).

$^1$H NMR (400 MHz, CDCl$_3$); δ6.48 (s, 1H); 7.24 (s, 1H); 7.30 (s, 1H); 7.36–7.40 (d, 1H); 7.46–7.48 (d, 1H); 7.6 (s, 1H); 7.8 (s, 1H).
Coumarin 20:

7-Bromo-4-(1-methylpyrrol-3-yl)coumarin

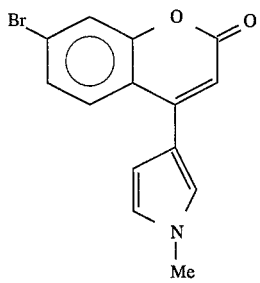

Step 1:

7-Bromo-4-(1-triisopropylsilyl-1H-pyrrol-3-yl)coumarin

The triflate from Coumarin 11, Step 1 (298 mg, 0.8 mmol) was mixed with 1-(triisopropylsilyl)-3-(tributylstannyl)pyrrole (451 mg, 0.88 mmol) (J. Org. Chem., 57, 1653, 1992) (Ph$_3$P)$_4$Pd (37 mg, 0.032 mmol) and LiCl (101.7 mg, 2.4 mmol) in dioxane (2.0 mL) and the mixture was heated at reflux for 2.5 h. The reaction mixture was diluted in EtOAc, washed with brine, dried over MgSO$_4$, filtered and evaporated to give an oil which was purified on a silica column using toluene as the eluent. The title compound was obtained as an oil (100 mg) (28%).

Step 2:

7-Bromo-4-(1-methylpyrrol-3-yl)coumarin

To a solution of the silyl compound from Step 1 (42 mg, 0.094 mmol) in THF (1 mL) was added n-Bu$_4$NF (1M) in THF (94 μL, 0.094 mmol) and the reaction mixture was stirred at r.t. for 15 min.. The mixture was diluted with EtOAc, washed with brine, dried over MgSO$_4$, filmed and evaporated to give an oil (27 mg, 100%) which was dissolved in DMF (1 mL). Sodium hydride (97%, 2.8 mg, 0.11 mmol) was added at r.t. and stirred for 15 min.. Then MeI (7 μL, 0.11 mmol) was added. The reaction mixture was stirred for 30 min. and then heated at 60° C. for 30 min.. The reaction mixture was then poured into H$_2$O and extracted with EtOAc. The combined organic phase was washed with brine, dried over MgSO$_4$, filtered and evaporated to give the title compound as an oil 29 mg (100% ).

$^1$H NMR (400 MHz, CDCl$_3$); δ3.75 (s, 3H); 6.3 (s, 1H); 6.4 (d, 1H); 6.72 (d, 1H); 6.95 (s, 1H); 7.2 (m, 2H); 7.92 (d, 1H).
Coumarin 21:

67

7-Bromo-4-(thiazol-4-yl)coumarin

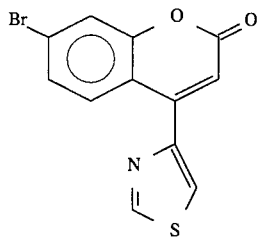

Step 1:

7-Bromo-4-(1-ethoxyvinyl)coumarin

A mixture of triflate (from Coumarin 11, Step 1) (2.88 g), (1-ethoxyvinyl) tributyltin (3.06 g), (Ph₃P)₄Pd (0.36 g) and LiCl (0.98 g) in dioxane (20 mL) was refluxed for 4 h. Ethyl acetate was then added and the organic phase was washed with H$_2$O and brine, dried (MgSO$_4$) and evaporated. Flash chromatrography of the residue (silica gel; hexane/EtOAc (9:1)) afforded the title compound as a yellow solid.

Step 2:

7-Bromo-4-(2-bromoacetyl)coumarin

To a solution of vinyl ether from Step 1 (1.02 g) in CH$_3$CN:H$_2$O 4:1 (25 mL) were successively added NBS (0.82 g) and concentrated HBr (20 μL). After being stirred at r.t. for 4 h, the reaction mixture was treated with 5% aqueous NaHSO$_3$ (1 mL). Ethyl acetate was then added and the organic phase was washed with saturated aqueous NaHCO$_3$, H$_2$O and brine, dried (MgSO$_4$) and evaporated. Flash chromatography of the residue (silica gel; hexane/EtOAc (85:15)) afforded the title compound as a white solid.

Step 3:

7-Bromo-4-(thiazol-4-yl)coumarin

Freshly prepared thioformamide (Helv. Chim. Acta, 31, 2065, 1948) (160 mg) was added to a solution of α-bromoketone from Step 2 (200 mg) in THF (5 mL) and the reaction mixture was stirred at r.t. for 2 h. Ethyl acetate was then added and the organic phase was washed with saturated aqueous NH$_4$Cl, H$_2$O and brine, dried (MgSO$_4$) and evaporated. Flash chromatography of the residue (silica gel; hexane/EtOAc (65:35) afforded the title compound as a white solid.

$^1$H NMR (400 MHz, CDCl$_3$); δ6.65 (s, 1H); 7.40 (d, 1H); 7.55 (s, 1H); 7.75 (s, 1H); 8.0 (d, 1H); 9.0 (s, 1H).

Coumarin 22:

7-Mercapto-4-(furan-3-yl)coumarin

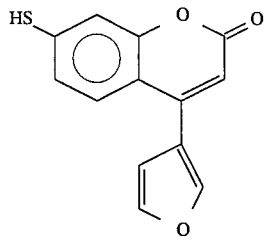

Step 1:

68

7-(2-Trimethylsilylethylthio)-4-(furan-3-yl)coumarin

A mixture of 7-bromo-4-(furan-3-yl)coumarin (Coumarin 4) (1.5 g, 5.15 mmol), 2-(trimethylsilyl)ethanethiol (830 mg, 6.18 mmol), and K$_2$CO$_3$ (1.77 g, 12.9 mmol) in 1-methyl-2-pyrrolidinone (12 mL) was heated at 105° C. for 4 h. After cooling, them was added saturated aqueous NH$_4$Cl (10 mL), then H$_2$O (50 mL) and the mixture was extracted twice with EtOAc. The organic extracts were washed 4 times with H$_2$O, dried over MgSO$_4$ and evaporated to a residue which was chromatographed on silica gel eluting with a 1:3 mixture of EtOAc and hexane, to afford the title compound (963 mg) as a tan solid.

Step 2:

7-Mercapto-4-(furan-3-yl)coumarin

The coumarin from Step 1 (963 mg) was dissolved in DMF (25 mL) and to this solution there was added n-Bu$_4$NF (1M) in THF (8.4 mL). The mixture was stirred at r.t. for 2 h, poured onto 1N aqueous HCl (50 mL), diluted with H$_2$O (50mL) and filtered to afford the title compound (620 mg) as a tan solid. m.p.: 167°–170° C.

PREPARATION OF NAPHTHALENES

Naphthalene 1:

3-Cyano-1-(furan-3-yl)-6-naphthol (U.S. Pat. No. 5,308,852, Merck Frosst)

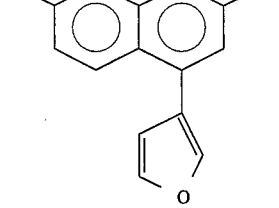

Naphthalene 2:

3-Cyano-1-phenyl-6-naphthol (U.S. Pat. No. 5,308,852, Merck Frosst)

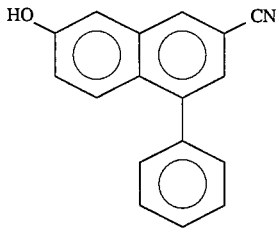

Naphthalene 3:

69

3-Cyano-1-(furan-3-yl)-6-hydroxymethylnaphthalene

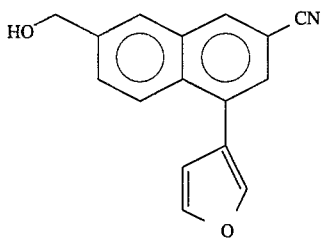

Step 1:

3-Cyano-1-(furan-3-yl)-6-(trifluoromethanesulfonyloxy)naphthalene

To a solution of the Naphthalene 1 (565 mg, 2.40 mmol) in $CH_2Cl_2$ (16 mL) at 0° C. was added pyridine (380 mg, 4.80 mmol, 389 μL) and triflic anhydride (813 mg, 2.88 mmol, 485 μL). The solution was stirred at 0° C. for 2.5 h and then poured into sat. aq. $NH_4Cl$. The layers were separated and the aq. phase extracted with EtOAc (3×30 mL). The combined organic layers were washed with 5% aq. HCl, 5% aq. $NaHCO_3$, brine, and dried over anhydrous $MgSO_4$. Evaporation of the solvent gave a solid (810 mg) which was used directly in the next step.

Step 2:

6-Carbomethoxy-3-cyano-1-(furan-3-yl)naphthalene

The crude triflate from Step 1 was dissolved in MeOH (8 mL) and DMSO (14 mL). To the mixture was added $Et_3N$ (4.8 mmol, 486 mg, 670 μL), Pd $(OAc)_2$ (0.24 mmol, 54 mg) and 1,1'-bis(diphenylphosphino)ferrocene (0.48 mmol, 266 mg) and stirred under CO atmosphere at 65° C. for 15 h. The mixture was poured into aq. sat. $NH_4Cl$, extracted with EtOAc (3×50 mL) and the combined organic layers washed with brine and dried over anhydrous $MgSO_4$. Evaporation of the solvent and flash chromatography (4% EtOAc in toluene) gave 450 mg of the title methyl ester.

Step 3:

3-Cyano-1-(furan-3-yl)-6-hydroxymethylnaphthalene

To a solution of the ester from Step 2 (450 mg, 1.62 mmol) in THF (10 mL) and MeOH (10 mL) was added $LiBH_4$ (3.24 mmol, 1.62 mL, 2.0M in THF). The mixture was stirred for 5h at r.t. and then poured into 100 mL 5% aq. HCl solution. The layers were separated and the aqueous phase was extracted with EtOAc (3×50 mL). The combined organic layers were washed with brine and dried over anhydrous $MgSO_4$. Evaporation of the solvent and flash chromatography (50% EtOAc in hexane) gave 300 mg of the title product.

Naphthalene 4:

70

3-Cyano-1-(furan-3-yl)-6-iodonaphthalene

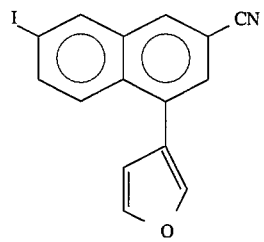

Step 1:

3-Cyano-1-(furan-3-yl)-7-trimethyltinnaphthalene

Following the procedure described for Coumarin 21, Step 1 but substituting 1-(3-furyl)-3-cyano-6-(trifluoromethanesulfonyloxy)naphthalene (from Naphthalene 3, Step 1) for the Comarin 11, Step 1 and hexamethylditin for (1-ethoxyvinyl) tributyltin as starting material, the title compound was obtained as a white solid.

Step 2:

3-Cyano-1-(furan-3-yl)-6-iodonaphthalene

A saturated solution of iodine in chloroform was added to a solution of compound from Step 1 (0.58 g) in $CHCl_3$ (2 mL) until a persistant purple coloration was obtained. The reaction mixture was stirred at r.t. for 1 h before it was washed with 10% aqueous $NaHSO_3$, $H_2O$ and brine, dried ($MgSO_4$) and evaporated. Flash chromatography of the residue (silica gel; hexane:EtOAc (95:5)) afforded the title compound as a white solid.

$^1H$ NMR (400 MHz, $CDCl_3$); δ6.65 (s, 1H); 7.60 (d, 2H); 7.65 (s, 1H); 7.85 (m, 2H); 8.05 (s, 1H); 8.30 (s, 1H).

Naphthalene 5:

3-Cyano-1-(furan-3-yl)-6-naphthalenethiol

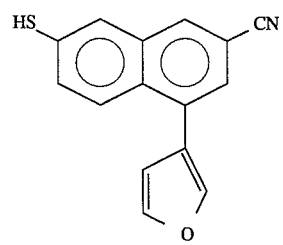

Step 1:

3-Cyano-1-(furan-3-yl)-6-[2-trimethylsilylethylthio]naphthalene

A mixture of 3-cyano-1-(furan-3-yl)-6-iodonaphthalene (2.5 g, 7.25 mmol), 2-(trimethylsilyl)ethanethiol (974 mg, 7.25 mmol), potassium tert-butoxide (1.624 g, 14.5 mmol) and $(Ph_3P)_4Pd$ (200 mg, 0.17 mmol) in EtOH (250 mL) was refluxed for 6.5 h. After evaporation of the EtOH, the residue was partitioned between $Et_2O$ and $H_2O$. The crude product from the organic phase was chromatographed on silica gel, eluting with a 1:9 mixture of EtOAc and hexane to afford the title product (1.8 g) as an amber oil.

Step 2:

3-Cyano-1-(furan-3-yl)-6-naphthalenethiol

The product from Step 1 (1.8 g) was dissolved in DMF (40 mL) and there was added n-Bu₄NF (1M) in THF (15 mL). The resulting mixture was stirred at r.t. for 1.5 h, diluted with 1N aqueous HCl (40 mL) then H₂O (300 mL) and filtered to afford the title thiol (1.06 g) as a light orange solid m.p.: 144°–146° C.

PREPARATION OF QUINOLINE INTERMEDIATE

Quinoline 1:

7-Bromomethyl-2-cyano-4-(furan-3-yl)quinoline

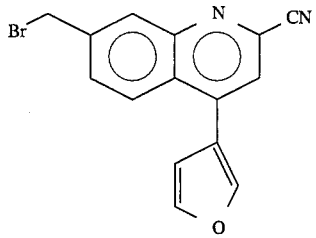

Step 1:

7-Chloro-4-iodoquinoline 4,7-Dichloroquinoline (50 g) (Aldrich) was added in small portions to HI (425 mL) at r.t. and then heated at 130° C. for 5 h. The mixture was cooled, poured into ice/H₂O (600 mL), made basic (pH 10) with 10N NaOH, and extracted with CHCl₃. The combined organics were washed with NH₄OAc buffer, 10% Na₂S₂O₃, brine, dried (Na₂SO₄) and concentrated providing the title compound which was used as such.

Step 2:

7-Chloro-4-(furan-3-yl)quinoline

To a solution of 3-bromofuran (30 g) in Et₂O (400 mL) at −78° C. was added n-BuLi (89.3 mL, 2.4M in hexane). After stirring for 40 min., (MeO)₃B (25.5 mL) was added and the mixture was stirred at −78° C. for 30 min. followed by 30 min. at 0° C. Na₂CO₃ (196 mL of a 2M solution) was then added and the mixture stirred at 0° C. for 3 h. The Et₂O was evaporated and replaced by THF (730 mL); 7-chloro-4-iodoquinoline (53.7 g) and (Ph₃P)₄Pd (10.7 g) were added and the mixture was heated at reflux for 12 h. The mixture was cooled to r.t., the layers were separated and the THF phase was concentrated. The aqueous phase was extracted with EtOAc, which was combined with the residue from the THF phase. The organics were washed with H₂O, brine, dried (MgSO₄) and concentrated. Chromatography (silica gel; EtOAc/hexane (1:9)) provided the title compound as a beige solid.

Step 3:

4-(Furan-3-yl)-7-methylquinoline

To a mixture of 7-chloro-4-(furan-3-yl)quinoline (30.2 g) and [1,3-bis(diphenylphosphino)propane]nickel (II) chloride (7.1 g) in Et₂O (950 mL) was added MeMgBr (141 mL, 1.4M in 3:1 THF:toluene) at such a rate to maintain a temperature of 30° C. The mixture was refluxed for 30 min., cooled to 0° C. and saturated NH₄Cl (200 mL) was added followed by H₂O (100 mL). The layers were separated and the aqueous phase was extracted with EtOAc. The combined organics were washed with NH₄OAc buffer, brine, dried (MgSO₄) and concentrated. Chromatography (silica gel;EtOAc/hexane (3:7)) provided the title compound as a beige oil.

Step 4:

2-Cyano-4-(furan-3-yl)-7-methylquinoline

To a solution of 4-(furan-3-yl)-7-methylquinoline (24.9 g) in CHCl₃ (900 mL) was added mCPBA (30.8 g; 80%) portionwise. After 1 h, saturated NaHCO₃ was added followed by H₂O (150 mL). The aqueous phase was extracted with CHCl₃ and the combined organics were washed with saturated NaHCO₃, brine, dried (Na₂SO₄) and concentrated. The residue was dissolved in CH₂Cl₂ (900 mL) and TMSCN (19 mL) was added. After 5 min., dimethylcarbamyl chloride (13.1 mL) was added and the mixture was stirred for 12 h at r.t. Potassium carbonate (10%; 400 mL) was slowly added and the aqueous layer was extracted with CH₂Cl₂. The combined organics were washed with 10% K₂CO₃, NH₄OAc buffer, brine, dried (Na₂SO₄) and concentrated. Chromatography (silica gel; EtOAc/hexane (1:9 to 2:3) provided the title compound as a solid.

Step 5:

7-Bromomethyl-2-cyano-4-(furan-3-yl)quinoline

To a solution of 2-cyano-4-(furan-3-yl)-7-methylquinoline (4.2 g) in refluxing CCl₄ (400 mL) was added NBS (3.3 g) and AIBN (150 mg) portionwise. After 90 min., the mixture was cooled to r.t. filtered through a pad of silica gel washing with CH₂Cl₂. The filtrate was concentrated and swished with Et₂O for 15 h. The solid precipitate was collected and was 85% of the title compound. This material was used as such in the subsequent reactions.

Quinoline 2:

7-Bromomethyl-2-cyano-4-(4-fluorophenyl)quinoline

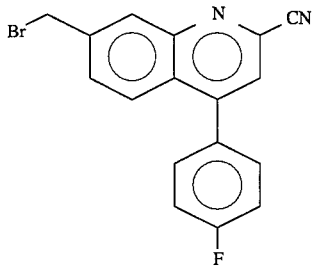

Step 1:

7-Chloro-4-(4-fluorophenyl)quinnoline

To a solution of 4-fluorophenylmagnesium bromide (5.2 mL, 10.4 mmol) 2M in Et₂O) in THF (8 mL) at r.t., was added dropwise a solution of 4,7-dichloroquinoline (Aldrich) (2.07 g, 10.47 mmol) and (Ph₃P)₄Pd (0.48 g, 0.42mmol) in THF (10mL). After 18 h, more 4-fluorophenyl magnesium bromide (1.5 mL) was added. The solution was stirred for 5 h, at r.t., then quenched with a saturated NH₄Cl solution. The aqueous phase was extracted with EtOAc (3×). The combined organic phase were dried (MgSO₄) and concentrated. Flash chromatography with EtOAc/hexane (1:5.6) provided the title compound (1.4 g 53%) as a solid.

Step 2:

7-Bromomethyl-2-cyano-4-(4-fluorophenyl)quinoline

Following the procedure described for Quinoline 1, Steps 3 to 5 but substituting 7-chloro-4-(4-fluorophenyl)quinoline from Step 1 for 7-chloro-4-(furan-3-yl)quinoline, the title compound was obtained.

$^1$H NMR (300 MHz, CDCl$_3$); δ4.66 (s, 2H); 7.23–7.29 (m, 2H); 7.43–7.48 (m, 2H); 7.60–7.69 (m, 2H); 7.91 (d, 1H); 8.18 (d, 1H).

PREPARATION OF ISOQUINOLINES

Isoquinoline 1:

7-Iodo-4-phenylisoquinoline

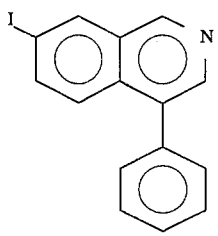

Step 1:

7-Methoxy-4-phenylisoquinoline

To a solution of 3-methoxybenzylamine (15 g) and pyridine (15 mL) in CH$_2$Cl$_2$ (100 mL) at 0° C. was added p-toluenesulfonyl chloride (21 g) portionwise. After addition was complete, the mixture was stirred at r.t. for 2 h and then saturated NH$_4$Cl was added. The mixture was extracted with Et$_2$O and the extracts were washed with H$_2$O, brine, dried (MgSO$_4$) and concentrated. The residue, 2-bromoacetophenone (23 g) and Cs$_2$CO$_3$ (45 g) in acetone (400 mL) were stirred at r.t. for 20 h. The acetone was evaporated and saturated NH$_4$Cl was added. The mixture was extracted with EtOAc and the organics were washed with H$_2$O, brine, dried (MgSO$_4$) and concentrated. The residual solid was swished in Et$_2$O for 3 h and then mixed with TFA (17 mL). After heating at 75° C. for 2.5 h, the mixture was cooled to r.t., EtOAc and H$_2$O were added and the aqueous phase was made basic by the careful addition of solid K$_2$CO$_3$. The organic phase was washed with saturated NaHCO$_3$, H$_2$O, brine and dried (MgSO$_4$). Concentration and chromatography (silica gel; hexane/EtOAc (3:2 to 1:1)) provided the title compound as a solid.

Step 2:

7-Trifluoromethanesulfonyloxy-4-phenylisoquinoline

A mixture of 7-methoxy-4-phenylisoquinoline (8.8 g) and pyridine hydrochloride (30 g) was heated at 195–200° C. for 4.5 h. The mixture was cooled and H$_2$O was added. After stirring for 30 min., the precipitate that formed was isolated by filtration, and washed with H$_2$O. The residual solid was swished with EtOAc for 90 min. To a portion of this material (3 g) and pyridine (5.5 mL) in CH$_2$Cl$_2$ (100 mL) at 0° C. was added triflic anhydride (2.8 mL) and the mixture was stirred at 0° C. for 30 min and then at r.t. for 90 min. Saturated NH$_4$Cl was added and the mixture extracted with CH$_2$Cl$_2$. The organics were washed with H$_2$O, brine, dried (MgSO$_4$) and concentrated. Chromatography (silica gel; hexane/EtOAc (4:1)) provided the title compound as a solid.

Step 3:

7-Iodo-4-phenylisoquinoline

A mixture of 7-trifluoromethanesulfonyloxy-4-phenylisoquinoline (2.7 g), hexamethylditin (7.4 g), LiCl (1.9 g) and (Ph$_3$P)$_4$Pd (500 mg) in dioxane (50 mL) was heated at 90° C. for 1 h. The mixture was cooled, filtered through celite and the filtrate was concentrated. The residual material was dissolved in CHCl$_3$ (50 mL) and I$_2$ (1.8 g) was added. After 1 h, 10% NaHSO$_3$ was added and the mixture was extracted with CHCl$_3$. The organics were washed with H$_2$O, brine, dried (MgSO$_4$) and concentrated. Chromatography (silica gel; hexane/EtOAc (10:1 to 7:3)) provided the title compound as an oil.

$^1$H NMR (300 MHz, Acetone-d$_6$); δ7.45–7.58 (m, 5H); 7.64 (d, 1H); 7.96 (d, 1H); 8.46 (s, 1H); 8.58 (d, 1H); 9.22 (s, 1H).

Isoquinoline 2:

7-Iodo-4-(furan-3-yl)isoquinoline

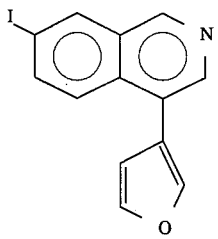

Step 1:

3-Chloroacetylfuran

Under N$_2$, 3-furoic acid (25 g, 0.22 mmol) was dissolved in CH$_2$Cl$_2$ (200 mL) and DMF (few drops) then oxalyl chloride (23.9 mL, 0.27 mmol) was added at 0° C. The resulting solution was stirred at 0° C. for 15 min. and at r.t. for 30 min. The solvent was evaporated. To the acid chloride (3.1 g, 24 mmol) in Et$_2$O (20 mL) at r.t. was added an ethereal solution of diazomethane until the reaction was completed by T.L.C. The reaction mixture was cooled to 0° C. and HCl (g) was bubbled in for 20 min.. Excess HCl (g) was removed by bubbling N$_2$ into the solution for 2 h. The resulting solution was washed with a saturated solution of NaHCO$_3$ (2×), brine, dried over MgSO$_4$ and then concentrated. Flash chromatography of the residue with hexane:EtOAc 9:1 as eluent afforded the title compound as a white solid.

Step 2:

7-Iodo-4-(furan-3-yl)isoquinoline

Following the same procedure as described for Isoquinoline 1, but substituting 3-chloroacetylfuran from Step 1 for 2-bromoacetophenone, the title compound was obtained.

$^1$H NMR (300 MHz, CDCl$_3$); δ6.61 (d, 1H); 7.54 (s, 1H); 7.62 (s, 1H); 7.71 (d, 1H); 7.80 (m, 1H); 8.27 (s, 1H); 8.46 (s, 1H); 8.99 (s, 1H).

EXAMPLE 1

7-[5-Fluoro-3-(3-hydroxypent-3-yl) phenoxymethyl]-4-(furan-3 -yl)coumarin

To a solution of Coumarin 1 (77 mg, 0.25 mmol), Phenol 2 (50 mg, 0.25 mmol) in dry DMF (5 mL) was added Cs$_2$CO$_3$ (99 mg, 0.3 mmol) and the resulting mixture was stirred at r.t. for 2 h. Then the reaction mixture was added to an aqueous solution of HCl (1N) and extracted with EtOAc. The combined organic layers were washed with brine, dried over MgSO$_4$ and evaporated. Purification by flash chromatography using toluene:EtOAc (9:1) gave 95 mg (89%) of the title product.

$^1$H NMR (400 MHz, CDCl$_3$); δ0.74 (t, J=7.5 Hz, 6H); 1.57 (s, 1H); 1.78 (m, 4H); 5.1 (s, 2H); 6.41 (s, 1H) 6.53 (dt, J=10.2 Hz, 1H); 6.66 (s, 1H); 6.67 (dt, 1H); 6.81 (s, 1H); 7.33 (m, 1H), 7.45 (s, 1H), 7.60 (s, 1H); 7.78 (m, 2H).

EXAMPLE 2

7-[5-Fluoro-3-(3-hydroxypent-3-yl)phenylthio]-4-(furan-3-yl)coumarin

The Thiophenol 3 (81 mg, 0.378 mmol), the Coumarin 4 (143 mg, 0.491 mmol) and K$_2$CO$_3$ (130 mg, 0.945 mmol) were heated at 145° C. in N-methyl-2-pyrrolidinone (2 mL) for 1 h. The mixture was allowed to cool to r.t. poured into H$_2$O (20 mL), and extracted with EtOAc (3×). The combined extracts were washed with 25% NH$_4$OAc buffer (1×), H$_2$O (2×), brine (1×), dried (MgSO$_4$) and concentrated. The brown residue obtained was purified by column chromatography on silica (EtOAc/hexane 1:4) to give a yellow foam (66 mg, 41%).

$^1$H NMR (300 MHz, Acetone-d$_6$); δ0.74 (t, 6H), 1.84 (m, 4H), 3.87 (s, 1H), 6.39 (s, 1H), 6.90 (m, 1H), 7.12–7.20 (m, 3H), 7.30 (m, 1H), 7.47 (t, 1H), 7.80–7.84 (m, 2H), 8.16 (s, 1H).

EXAMPLES 12–13

7-[5-Fluoro-3-(hexafluoro-2-hydroxyprop-2-yl)phenylsulfonyl]-4-(4-fluorophenyl)coumarin (Ex. 12) and 7-[5-fluoro-3-(hexafluoro-2-hydroxyprop-2-yl)phenylsulfinyl]-4-(4-fluorophenyl)coumarin (Ex. 13)

To a solution of Example 4 (100 mg, 0.19 mmol) in CH$_2$Cl$_2$ (5 mL) at 0° C. was added mCPBA (65 mg) and the reaction mixture was stirred for 1 h. Then CH$_2$Cl$_2$ was added and washed with an aqueous solution of 10% NaOH, H$_2$O and brine, dried over MgSO$_4$ and evaporated. Purification by flash chromatography using toluene:EtOAc 85:15 gave 72 mg of the corresponding sulfone and 20 mg of the sulfoxide. Example 12; Mass spec.; 565 (MH$^+$); Example 13; Mass spec.; 549 (MH$^+$).

EXAMPLE 22

7-{5-Fluoro-3-[1-hydroxy-1-(thiazol-2-yl)-2,2,2-trifluoroethyl]phenylthio}-4-(4-fluorophenyl)coumarin Step 1:

7-[5-Fluoro-3-(thiazol-2-ylcarbonyl)phenylthio]-4-(4-fluorophenyl)coumarin

Following the procedure described for Example 2 but substituting Thiophenol 5 for Thiophenol 3 and Coumarin 7 for Coumarin 4 as starting material the title compound was obtained.
Step 2:

7-{5-Fluoro-3-[1-hydroxy-1-(thiazol-2-yl)-2,2,2-trifluoroethyl]phenylthio}-4-(4-fluorophenyl)coumarin Following the procedure described for the preparation of Thiophenol 4, Step 1 but substituting the ketone from Step 1 for 3,5 -difluorobenzophenone as starting material the title compound was obtained. m.p.: 72°–73° C.

EXAMPLE 26

7-{5-Fluoro-3-[1-hydroxy-1-(imidazol-2-yl)propyl]phenoxymethyl}-4-(furan-3-yl)coumarin Step 1:

7-(5-Fluoro-3-{1-hydroxy-1-[N-(2-trimethylsilylethoxymethyl)imidazol-2-yl]propyl}phenoxymethyl)-4-(furan-3-yl)coumarin Following the procedure described for Example 1, but substituting Phenol 6 for Phenol 2 as starting material, the title compound was obtained.
Step 2:

7-{5-Fluoro-3-[1-hydroxy-1-(imidazol-2-yl)propyl]phenoxymethyl}-4-(furan-3-yl)coumarin Under N$_2$ the compound from Step 1 (94 mg, 0.159 mmol) was dissolved in THF (2 mL). Tetrabutylammonium fluoride was added ((795 μL, 0.795 mmol) and the reaction was stirred at 55° C. for 1 h. Ethyl acetate was added and the organic phase was washed with brine, dried over MgSO$_4$, filtered and evaporated to give an oil which was purified by a flash silica column using EtOAc then 5% MeOH in CH$_2$Cl$_2$ as the eluent. The title compound was obtained: 12.8 mg (17%). Mass spec.: 461 (MH$^+$).

EXAMPLE 44

7-[5-Fluoro-3-(hexafluoro-2-methoxyprop-2-yl)phenylthio]-4-(furan-3 -yl)coumarin Following the procedure described for Alcohol 5, Step 2 but substituting compound from Example 3 for 6-[1-Hydroxy-1-(thiazol-2 -yl)propyl]-(O-tertbutyldimethylsilyl)pyridin-2-yl methanol as starting material the title compound is obtained.

EXAMPLE 45

7-[5-Fluoro-3-(hexafluoro-2-methoxyprop-2-yl)phenylthio]-4-(4-fluorophenyl)coumarin Following the procedure described for Alcohol 5, Step 2 but substituting compound from Example 4 for 6-[1-Hydroxy-1-(thiazol-2 -yl)propyl]-(O-tertbutyldimethylsilyl)pyrdidin-2-yl methanol as starting material the title compound is obtained.

EXAMPLE 46

3-Cyano-1-(furan-3-yl)-6-[6-(3-hydroxypent-3-yl)pyridin-2-ylmethoxy]naphthalene To a mixture of Naphthalene 1 (125 mg, 0.53 mmol), Alcohol 2 (94.3 mg), 0.48 mmol) and triphenylphosphine (164 mg, 0.62 mmol) in THF (10 mL) was added di-tert-butylazodicarboxylate (144 mg, 0.62 mmol) and the mixture was stirred at r.t. for 1 h. After evaporation of the THF, the residue was chromatographed on a column of silica gel,

EXAMPLE 53

3-Cyano-1-(furan-3-yl)-6-{5-fluoro-3-[1-hydroxy-1-(thiazol-2-yl)propyl]phenylthio}naphthalene Following the procedure described for Naphthalene 5, Step 1, but substituting Thiophenol 8 for 2-(trimethylsilyl)ethanethiol as starting material, the title compound was obtained. m.p.: 120°–122° C.

EXAMPLE 54

3-Cyano-1-(furan-3-yl)-6-{6-[1-hydroxy-1-(thiazol-2-yl)propyl]pyridin-2-yloxymethyl}naphthalene A mixture of the Bromopyridine 3 (108 mg, 0.38 mmol), Naphthalene 3 (104 mg, 0.42 mmol) 18-crown-6 (4.0 mg, 0.015 mmol) and NaOH (64 mg, 1.14 mmol) in 7 mL toluene was heated at reflux with a Dean-stark trap for 2 h. Additional NaOH (32 mg, 0.57 mmol) was added and the mixture was further heated at reflux for 3 h. The cooled solution was partitioned between aq. NH$_4$Cl and EtOAc and the aq. phase was extracted with EtOAc (2×30 mL). The combined organic layers were washed with brine and dried over anhydride MgSO$_4$. The solvent was evaporated and the residue chromatographed on silica gel using hexane EtOAc (7:3) to give 72 mg ot the title product.

Analysis calc'd for C, 69.36; H, 4.53; N, 8.99. Found: C, 69.43; H, 4.53; N, 8.85.

EXAMPLE 58

3-Cyano-1-(furan-3-yl)-6-{3-[1-methoxy-1-(thiazol-2-yl)propyl]phenoxymethyl}naphthalene Following the procedure described for Example 46 but substituting Naphthalene 3 for Naphthalene 1 and 3-[1-methoxy-1-(thiazol-2-yl)propyl]phenol (*J. Med. Chem* 1991, 34, 2176) as starting material, the title compound was obtained. m.p.: 156°–157° C.

EXAMPLE 64

7-[5-Fluoro-3-(hexafluoro-2-methoxyprop-2-yl)phenoxymethyl]-2-cyano-4-(furan-3-yl)quinoline Following the procedure described for Example 1 and for Alcohol 5, Step 2 but substituting Quinoline 1 for Coumarin 1 and Phenol 3 for Phenol 2 as starting material, the title compound is obtained. The following examples have been prepared according to the example referenced in each case, by coupling the identified components.

Compounds of the following examples were prepared using the starting materials and according to general procedures described in the examples specified within the parenthesis. Characterizing properties are also provided for each compound.

Example 3: (Ex. 2; Thiophenol 1, Coumarin 4); Mass spec.: 505 (MH$^+$).

Example 4: (Ex. 2; Thiophenol 1, Coumarin 7); $^1$H NMR (400 MHz, CDCl$_3$); δ3.69 (s, 1H); 6.30 (s, 1H); 7.07 (m, 1H); 7.2 (m, 4H); 7.4 (m, 4H); 7.6 (s, 1H).

Example 5: (Ex. 2; Thiophenol 1, Coumarin 15); Mass spec.: 516 (MH$^+$).

Example 6: (Ex. 2; Thiophenol 1, Coumarin 9); Mass spec.: 522 (MH$^+$).

Example 7: (Ex. 2; Thiophenol 1, Coumarin 21); Mass spec.: 522 (MH$^+$).

Example 8: (Ex. 2; Thiophenol 1, Coumarin 16); Mass spec.: 516 (MH$^+$).

Example 9: (Ex. 1; Phenol 3, Coumarin 2); m.p.: 172°–173° C.

Example 10: (Ex. 2; Bromopyridine 1, Coumarin 22); $^1$H NMR (400 MHz, Acetone-d$_6$); δ6.55 (s, 1H); 6.96 (s, 1H); 7.05 (br-s, 1H); 7.56 (m, 2H); 7.66 (s, 1H); 7.70 (d, 1H), 7.86 (s, 1H), 8.03 (m, 2H), 8.23 (s, 1H).

Example 11: (Ex. 1; Phenol 5, Coumarin 2); m.p. 86°–87.5° C.

Example 14: (Ex. 2; Thiophenol 1, Coumarin 8); m.p.: 165°–167° C.; Mass spec.: 550 (MH$^+$).

Example 15: (Ex. 2; Thiophenol 1, Coumarin 11); Mass spec.: 583 (MH$^+$).

Example 16: (Ex. 2: Bromopyridine 1, Coumarin 7); m.p.: 108°–111° C.

Example 17: (Ex. 2; Thiophenol 1, Coumarin 17); m.p.: 132°–134° C.

Example 18: (Ex. 2, Thiophenol 1, Coumarin 20); Mass spec.: 518 (MH$^+$).

Example 19: (Ex. 2; Thiophenol 1, Coumarin 6); Mass spec.: 515 (MH$^+$).

Example 20: (Ex. 2; Thiophenol 1, Coumarin 19); Mass spec.: 505 (MH$^+$).

Example 21: (Ex. 2; Thiophenol 4, Coumarin 4); Mass spec.: 513 (MH$^+$).

Example 23: (Ex. 2; Thiophenol 9, Coumarin 4); Mass spec.: 473 (MH$^+$).

Example 24: (Ex. 2; Thiophenol 6, Coumarin 4); m.p.: 75°–76° C.

Example 25: (Ex. 2; Thiophenol 7, Coumarin 4); m.p.: 72°–73° C.

Example 27: (Ex. 1; Phenol 11, Coumarin 1); Mass spec.: 454 (MH$^+$).

Example 28: (Ex. 1; Phenol 1, Coumarin 3); Mass spec.: 494 (MH$^+$).

Example 29: (Ex. 1; Phenol 1, Comarin 1); $^1$H NMR (400 MHz, CDCl$_3$); δ0.88 (t, J=7.3 Hz, 3H); 2.33 (m, 2H); 3.51 (s, 1H); 5.12 (s, 2H); 6.41 (s, 1H), 6.54 (d, J=10.1 Hz, 1H); 6.66 (s, 1H); 6.95 (d, J=9.8 Hz, 1H); 7.05 (s, 1H); 7.26 (d, J=3.1 Hz, 1H); 7.31 (d, J=8.1 Hz, 1H); 7.42 (s, 1H); 7.59 (s, 1H); 7.69 (d, J=3.1 Hz, 1H); 7.75 (d, J=8.3 Hz, 1H); 7.79 (s, 1H).

Example 30: (Ex. 1; Phenol 1, Coumarin 2); $^1$H NMR (400 MHz, CDCl$_3$); δ0.88 (t, J=7.3 Hz, 3H); 2.33 (m, 2H); 3.52 (s, 1H); 5.11 (s, 2H); 6.34 (s, 1H), 6.55 (d, 1H); 6.95 (d, J=9.8 Hz, 1H); 7.05 (s, 1 H); 7.24 (m, 4H); 7.44 (m, 4H); 7.69 (d, J=3.1 Hz, 1H).

Example 31: (Ex. 12; Thiophenol 8, Coumarin 4); Mass spec.: 512 (MH$^+$).

Example 32: (Ex. 2; Thiophenol 8, Coumarin 10); m.p.: 73°–74° C.

Example 33: (Ex. 2; Thiophenol 8, Coumarin 5); Mass spec.: 496 (MH$^+$).

Example 34: (Ex. 2; Thiophenol 8, Coumarin 6); Mass spec.: 490 (MH$^+$).

Example 35: (Ex. 2; Thiophenol 8, Coumarin 4); Mass spec.: 480 (MH$^+$).

Example 36: (Ex. 2; Thiophenol 8, Coumarin 7); Mass spec.: 508 (MH$^+$).

Example 37: (Ex. 1; Phenol 7, Coumarin 1); m.p.: 103°–104° C.

Example 38: (Ex. 1; Phenol 7, Coumarin 3); m.p. 97°–98° C.
Example 39: (Ex. 2; Thiophenol 1, Coumarin 13); m.p.: 89°–90° C.
Example 40: (Ex. 2; Thiophenol 1, Coumarin 12); Mass spec.: 567 (MH$^+$).
Example 41: (Ex. 2; Thiophenol 10, Coumarin 7); Mass spec.: 633 (MH$^+$).
Example 42: (Ex. 2; Thiophenol 1, Coumarin 18); m.p.: 119°–120° C.
Example 43: (Ex. 2; Thiophenol 1, Coumarin 14); m.p.: 56°–57° C.
Example 47: (Ex. 46; Phenol 2, Naphthalene 3); Mass spec.: 430 (MH$^+$).
Example 48: (Ex. 2; Bromopyridine 2, Naphthalene 5); Mass spec.: 415 (MH$^+$).
Example 49: (Ex. 46; Alcohol 3, Naphthalene 1); m.p.: 161°–162° C.
Example 50: (Ex. 46; Alcohol 3, Naphthalene 2); m.p.: 157°–159° C.
Example 51: (Ex. 2; Bromopyridine 1, Naphthalene 5); $^1$H NMR (400 MHz, Acetone-d$_6$); δ6.93 (s, 1H), 6.97 (s, 1H); 7.47 (d, 1H); 7.66 (d, 1H); 7.87 (m, 3H); 8.00 (t, 1H); 8.05 (s, 1H); 8.38 (d, 1H); 8.50 (d, 2H).
Example 52: (Ex. 2; Bromopyridine 3, Naphthalene 5); Mass spec.: 470 (MH$^+$).
Example 55: (Ex. 46; Alcohol 4; Naphthalene 1); m.p.: 130°–132° C.
Example 56: (Ex. 46; Alcohol 5, Naphthalene 1); m.p.: 155°–156° C.
Example 57: (Ex. 46; Phenol 7, Naphthalene 3); Analysis calc'd for C; 72.08; H, 4.75; N, 6.00; found C, 72.13; H, 4.82; N, 5.82.
Example 59: (Ex. 46; Alcohol 1, Naphthalene 1); m.p.: 140°–142° C.
Example 60: (Ex. 1; Phenol 13, Quinoline 1); m.p.: 116°–117° C.
Example 61: (Ex. 1; Phenol 14, Quinoline 1); m.p.: 90°–91° C.
Example 62: (Ex. 1; 3-Hydroxylbenzyl alcohol, Quinoline 1); m.p.: 136°–139° C.
Example 63: (Ex. 1; Phenol 9, Quinoline 1); Mass spec.: 427 (MH$^+$).
Example 65: (Ex. 1; Phenol 10, Quinoline 1); Mass spec.: 441 (MH$^+$).
Example 66: (Ex. 1; Phenol 14, Quinoline 1); m.p.: 112°–113° C.
Example 67: (Ex. 1; Phenol 3, Quinoline 1); m.p.: 173°–174° C.
Example 68: (Ex. 1; Phenol 3, Quinoline 2); m.p.: 169°–170° C.
Example 69: (Ex. 1; Phenol 4, Quinoline 1); Mass spec.: 527 (MH$^+$).
Example 70: (Ex. 1; Phenol 11, Quinoline 1); Mass spec.: 462 (MH$^+$).
Example 71: (Ex. 1; Phenol 12, Quinoline 1); $^1$H NMR (300 MHz, Acetone-d$_6$); δ0.80 (t, 3H); 2.16 (q, 2H); 4.28 (s, 1H); 5.41 (s, 2H); 6.35 (d, 1H); 6.93 (dd, 1H); 7.06 (s, 1H), 7.08 (d, 1H); 7.22–7.27 (m, 2H); 7.38 (m, 1H); 7.43 (s, 1H); 7.88 (s, 1H); 7.91 (d, 1H); 7.95 (s, 1H); 8.24 (m, 2H); 8.38 (d, 1H).
Example 72: (Ex. 1; Phenol 8, Quinoline 1); m.p. 123°–125° C.; Mass spec.: 443 (MH$^+$).
Example 73: (Ex. 1; Phenol 1, Quinoline 1); Mass spec.: 486 (MH$^+$).
Example 74: (Ex. 1; Phenol 7, Quinoline 1); m.p.: 136°–137° C.
Example 75: (Ex. 2; Thiophenol 1, Isoquinoline 1); $^1$H NMR (300 MHz, Acetone-d$_6$,); δ6.88 (dd, 1H); 7.30 (dq, 1H); 7.44 (brd, 1H); 7.61 (s, 1H); 7.76–7.83 (m, 2H); 7.99 (s, 2H); 8.20 (d, 1H); 8.29 (d, 1H); 8.56 (s, 1H); 9.22 (s, 1H).
Example 76: (Ex. 2; Thiophenol 1, Isoquinoline 2); $^1$H NMR (300 MHz, Acetone-d$_6$,); δ7.29 (m, 1H); 7.44 (d, 1H); 7.48–7.62 (m, 6H); 7.73 (dd, 1H), 7.94 (d, 1H); 8.09 (s, 1H); 8.30 (s, 1H); 8.46 (s, 1H); 9.28 (s, 1H).
Example 77: (Ex. 2; Thiophenol 8, Isoquinoline 1); m.p.: 134°–135° C.; Mass spec.: 463 (MH$^+$).

What is claimed is:

1. A compound having the formula $$R^1R^2C(OR^3)-Ar^1-X-Ar^2-Ar^3 \qquad I$$

wherein
Ar$^1$ is phenylene substituted with one or two of the same or different R$^4$ groups;
Ar$^2$ is 2H-1-benzopyran-2-one substituted with one or two of the same or different R$^5$ groups;
Ar$^3$ is phenyl substituted with one or two of the same or different R$^6$ groups;
X is S, S(O), or S(O)$_2$;
R$^1$ is H, lower alkyl, or lower perfluoroalkyl;
R$^2$ is H, lower alkyl or lower perfluoroalkyl;
R$^3$ is H or lower alkyl;
R$^4$ is H, lower alkyl, lower alkoxy, lower alkylthio, NO$_2$, CN, CF$_3$, CF$_3$O or halogen;
R$^5$ is R$^4$, oxo or thioxo;
R$^6$ is R$^4$, lower alkylsulfinyl, lower alkylsulfonyl or CO$_2$R$^7$;
R$^7$ is H or lower alkyl;
or a pharmaceutically acceptable salt thereof.

2. A compound of claim 1 wherein:
Ar$^1$ is phenylene which is unsubstituted or substituted with halogen;
Ar$^2$ is 2H-1-benzopyran-2-one;
Ar$^3$ is phenyl substituted with one or two of the same or different R$^6$ groups;
X is S, S(O) or S(O)$_2$;
R$^1$ is H, lower alkyl, or lower perfluoroalkyl;
R$^6$ is R$^4$.

3. A compound of claim 1 having the Formula Ia

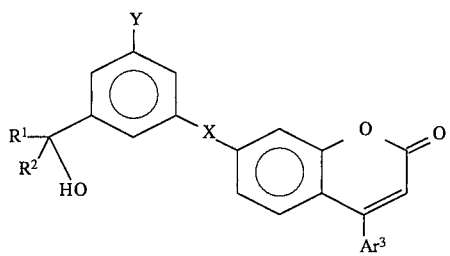

wherein:
Ar$^3$ is phenyl optionally substituted with one or two of the same or different halogen atoms, or with one nitro group;
X is S, S(O)$_2$, S(O);
Y is H or F;
R$^1$ is lower alkyl, or perfluoro lower alkyl;
R$^2$ is H, lower alkyl, or lower perfluoroalkyl.

4. A pharmaceutical composition comprising a therapeutically effective amount of a compound of claim 1 and a pharmaceutically acceptable carrier.

5. A method of preventing the synthesis, the action, or the release of SRS-A or leukotrienes in a mammal which comprises administering to said mammal an effective amount of a compound of claim 1.

6. The method of claim 5 wherein the mammal is man.

7. A method of treating asthma in a mammal comprising administering to a mammal in need of such treatment a therapeutically effective amount of a compound of claim 1.

8. A method of treating inflammatory diseases of the eye in a mammal which comprises administering to a mammal in need of such treatment a therapeutically effective amount of a compound of claim 1.

9. The method of claim 8 wherein the mammal is man.

* * * * *